United States Patent
Harrington et al.

(10) Patent No.: US 10,196,343 B2
(45) Date of Patent: Feb. 5, 2019

(54) HYDROGEN SULFIDE SCAVENGERS

(71) Applicant: ECOLAB USA INC., St. Paul, MN (US)

(72) Inventors: Ryan Matthew Harrington, Houston, TX (US); Prakasa Rao Anantaneni, Richmond, TX (US); Lawrence J. Karas, Missouri City, TX (US); Kekeli Ekoue-Kovi, Sugar Land, TX (US)

(73) Assignee: ECOLAB USA INC., St. Paul, MN (US)

( * ) Notice: Subject to any disclaimer, the term of this patent is extended or adjusted under 35 U.S.C. 154(b) by 0 days.

(21) Appl. No.: 15/346,719

(22) Filed: Nov. 8, 2016

(65) Prior Publication Data

US 2017/0088505 A1    Mar. 30, 2017

Related U.S. Application Data

(62) Division of application No. 14/168,594, filed on Jan. 30, 2014, now Pat. No. 9,523,045.

(60) Provisional application No. 61/758,478, filed on Jan. 30, 2013.

(51) Int. Cl.
| | |
|---|---|
| C07C 217/08 | (2006.01) |
| C10G 29/20 | (2006.01) |
| B01D 53/14 | (2006.01) |
| B01D 53/52 | (2006.01) |
| C10L 3/10 | (2006.01) |

(52) U.S. Cl.
CPC ........ *C07C 217/08* (2013.01); *B01D 53/1468* (2013.01); *B01D 53/1493* (2013.01); *B01D 53/52* (2013.01); *C10G 29/20* (2013.01); *C10L 3/103* (2013.01); B01D 2252/20405 (2013.01); B01D 2252/20426 (2013.01); B01D 2252/20431 (2013.01); B01D 2252/20484 (2013.01); B01D 2252/20489 (2013.01); B01D 2252/502 (2013.01); B01D 2252/504 (2013.01); B01D 2252/606 (2013.01); B01D 2256/24 (2013.01); B01D 2257/306 (2013.01); C10G 2300/207 (2013.01); C10L 2230/02 (2013.01); C10L 2290/541 (2013.01)

(58) Field of Classification Search
CPC .. C10G 2300/207; C10G 29/20; C10G 21/00; C10G 21/06; C10G 21/12; C10G 21/16; C10G 21/20
See application file for complete search history.

(56) References Cited

U.S. PATENT DOCUMENTS

| | | |
|---|---|---|
| 3,071,433 A | 1/1963 | Dunn |
| 3,458,444 A | 7/1969 | Shepherd et al. |
| 3,519,691 A | 7/1970 | von Portatius |
| 3,855,210 A | 12/1974 | Keller |
| 3,880,784 A | 4/1975 | Wagner et al. |
| 3,888,668 A | 6/1975 | Keller |
| 4,036,942 A | 7/1977 | Sibeud et al. |
| 4,107,106 A | 8/1978 | Dunleavy et al. |
| 4,195,151 A | 3/1980 | Dunleavy et al. |
| 4,327,092 A | 4/1982 | Collington et al. |
| 4,342,756 A | 8/1982 | Collington et al. |
| 4,410,436 A | 10/1983 | Holstedt et al. |
| 4,412,928 A | 11/1983 | Holstedt et al. |
| 4,557,843 A | 12/1985 | Holstedt et al. |
| 4,623,474 A | 11/1986 | Holstedt et al. |
| 4,627,930 A | 12/1986 | Holstedt et al. |
| 4,629,579 A | 12/1986 | Jessup et al. |
| 4,629,580 A | 12/1986 | Holstedt et al. |
| 4,657,686 A | 4/1987 | Holstedt et al. |
| 4,680,127 A | 7/1987 | Edmondson |
| 4,724,099 A | 2/1988 | Holstedt et al. |
| 4,756,842 A | 7/1988 | Holstedt et al. |
| 4,760,133 A | 7/1988 | Niwa et al. |
| 4,801,729 A | 1/1989 | Holstedt et al. |
| 4,892,670 A | 1/1990 | Mendelson |
| 5,213,680 A | 5/1993 | Kremer et al. |
| 5,304,361 A | 4/1994 | Parisi |
| 5,700,438 A | 12/1997 | Miller |
| 6,048,968 A | 4/2000 | Etzbach et al. |
| 6,267,913 B1 | 7/2001 | Marder et al. |
| 6,544,492 B1 | 4/2003 | DeBerry |
| 6,608,228 B1 | 8/2003 | Cumpston et al. |
| 7,078,005 B2 | 7/2006 | Smith et al. |
| 7,235,194 B2 | 6/2007 | Cumpston et al. |
| 7,438,877 B2 | 10/2008 | Salma et al. |
| 7,781,187 B2 | 8/2010 | Gasper et al. |
| 8,173,635 B2 | 5/2012 | Jimenez et al. |
| 8,197,722 B2 | 6/2012 | Marder et al. |
| 8,367,697 B2 | 2/2013 | Jimenez et al. |
| 8,597,549 B2 | 12/2013 | Cumpston et al. |
| 8,734,637 B2 | 5/2014 | Taylor |
| 2002/0185634 A1 | 12/2002 | Marder et al. |
| 2004/0086443 A1 | 5/2004 | Schield et al. |
| 2004/0096382 A1 | 5/2004 | Smith et al. |
| 2004/0110984 A1 | 6/2004 | Cumpston et al. |

(Continued)

FOREIGN PATENT DOCUMENTS

| | | |
|---|---|---|
| CA | 1257606 A | 7/1989 |
| CA | 1283397 C | 4/1991 |

(Continued)

OTHER PUBLICATIONS

STN search dated Mar. 4, 2016.*

(Continued)

*Primary Examiner* — Renee Robinson
*Assistant Examiner* — Derek N Mueller
(74) *Attorney, Agent, or Firm* — Eric D. Babych; Brinks Gilson & Lione

(57) ABSTRACT

Disclosed herein are scavenging compounds and compositions useful in applications relating to the production, transportation, storage, and separation of crude oil and natural gas. Also disclosed herein are methods of using the compounds and compositions as scavengers, particularly in applications relating to the production, transportation, storage, and separation of crude oil and natural gas.

3 Claims, No Drawings

(56) References Cited

U.S. PATENT DOCUMENTS

| | | |
|---|---|---|
| 2007/0154980 A1 | 7/2007 | Gasper et al. |
| 2008/0283804 A1 | 11/2008 | Cumpston et al. |
| 2009/0291937 A1 | 11/2009 | Jimenez et al. |
| 2011/0031165 A1 | 2/2011 | Karas et al. |
| 2011/0155646 A1 | 6/2011 | Karas et al. |
| 2012/0149680 A1 | 6/2012 | Jimenez et al. |
| 2013/0172623 A1 | 7/2013 | Kaplan |
| 2013/0240409 A1 | 9/2013 | Subramaniyam |
| 2013/0274426 A1 | 10/2013 | Sugiura et al. |
| 2013/0299734 A1 | 11/2013 | Yang et al. |
| 2014/0041893 A1 | 2/2014 | Adams et al. |
| 2014/0166282 A1 | 6/2014 | Martinez et al. |
| 2014/0166288 A1 | 6/2014 | Bailey et al. |
| 2014/0166289 A1 | 6/2014 | Martinez et al. |
| 2014/0190870 A1 | 7/2014 | Lehrer et al. |
| 2014/0209510 A1 | 7/2014 | Harrington et al. |
| 2014/0234191 A1 | 8/2014 | Laroche et al. |
| 2015/0175877 A1 | 6/2015 | Shindgikar et al. |
| 2017/0066977 A1 | 3/2017 | Rana et al. |

FOREIGN PATENT DOCUMENTS

| | | |
|---|---|---|
| CN | 1757796 A | 4/2006 |
| CN | 1814595 A | 8/2006 |
| CN | 1309868 C | 4/2007 |
| CN | 101037541 A | 9/2007 |
| CN | 100503595 C | 6/2009 |
| CN | 102993047 A | 3/2013 |
| CN | 103012199 A | 4/2013 |
| CN | 103018237 A | 4/2013 |
| CN | 103691277 A | 4/2014 |
| CN | 102993047 B | 9/2014 |
| CN | 103018237 B | 9/2014 |
| DE | 2729918 A1 | 1/1979 |
| DE | 3301822 A1 | 8/1983 |
| DE | 3925256 A1 | 1/1991 |
| DE | 19820400 A1 | 11/1999 |
| EP | 411409 A1 | 2/1991 |
| EP | 955342 B1 | 7/2001 |
| EP | 1363985 B1 | 8/2007 |
| EP | 2364768 A1 | 9/2011 |
| GB | 1107057 | 3/1968 |
| GB | 1107244 | 3/1968 |
| GB | 2114144 B | 7/1985 |
| JP | S58129059 A | 8/1983 |
| JP | H01271416 A | 10/1989 |
| JP | H03099038 A | 4/1991 |
| JP | 2000026746 A | 1/2000 |
| JP | 2006219506 A | 8/2006 |
| JP | 2009522406 A | 6/2009 |
| JP | 2011038215 A | 2/2011 |
| JP | 5441053 B2 | 3/2014 |
| PL | 144233 B1 | 4/1988 |
| RU | 2246342 C1 | 2/2005 |
| RU | 2008122310 A | 12/2009 |
| RU | 2009143509 A | 5/2011 |
| WO | WO 98/21521 A1 | 5/1998 |
| WO | WO 02/051968 A1 | 7/2002 |
| WO | WO 2007/078926 A2 | 7/2007 |
| WO | WO 2008/027721 A1 | 3/2008 |
| WO | WO 2008/155333 A1 | 12/2008 |
| WO | WO 2014/025577 A1 | 2/2014 |
| WO | WO 2012/086189 A1 | 5/2014 |
| WO | WO 2016/100224 A2 | 6/2016 |

OTHER PUBLICATIONS

STN search dated Mar. 6, 2018.*
STN Search dated Aug. 29, 2018 (Year: 2018).*
Bakke, Jan M. and Buhaug, Janne B. "Hydrogen Sulfide Scavenging by 1,3,5-Triazinanes. Comparison of the Rates of Reaction." Industrial & Engineering Chemistry Research (2004), vol. 43, pp. 1962-1965.
Kozyukov, V.P. and V.F. Mironov. Journal of General Chemistry of the USSR, Translated from Russian. New York: Consultants Bureau, 1982, pp. 1222-1229.
Pudovik et al. Journal of General Chemistry of the USSR, Translated from Russian. New York: Consultants Bureau, 1990, pp. 407-408.
International Search Report and Written Opinion from PCT/US2014/013818, dated May 28, 2014, 11 pages.
CAS Registry No. 120-07-0, entered STN: Nov. 16, 1984, 2 pages.
CAS Registry No. 3077-12-1, entered STN: Nov. 16, 1984, 2 pages.
CAS Registry No. 30525-89-4, entered STN: Nov. 16, 1984, 2 pages.
CAS Registry No. 50-00-0, entered STN: Nov. 16, 1984, 2 pages.
International Search Report and Written Opinion for International Application No. PCT/US2016/046813, 10 pages (dated Nov. 23, 2016).
International Search Report and Written Opinion for International Application No. PCT/US2016/046832, 9 pages (dated Nov. 23, 2016).
Kreulen, C.A. Smolders, G.F. Versteeg, and W.P.M. Swaaij, "Selective removal of $H_2S$ from sour gases with microporous membranes. Part II. A liquid membrane of water-free tertiary amines," Journal of Membrane Science 82 (1993) pp. 185-197.
International Search Report and Written Opinion for PCT/US2016/028534, dated Jun. 30, 2016, 12 pages.
International Search Report and Written Opinion for PCT/US2016/046813, dated Nov. 23, 2016, 10 pages.
International Search Report and Written Opinion for PCT/US2017/044099, dated Oct. 26, 2017, 11 pages.
European Search Report for European Application No. 16783814.3, 8 pages (dated Oct. 2, 2018).
Benn, M.H., et al., "Cytotoxic compounds. I. p-(N,N-di-2-chloroethyl)- and p-(N,N-di-2-bromoethylamino)thiophenol," Journal of the Chemical Society, 2800-10 (1958).
Bennett, E. O., "Corrosion inhibitors as preservatives for metalworking fluids—ethanolamines," Lubrication Engineering, 35(3):137-44 (1979).
Bradshaw, Jerald S., "Synthesis of macrocylic acetals containing lipophilic substituents," Tetrahedron, 43(19):4271-6 (1987).
Clerici, A., et al., "A New One-Pot, Four-Component Synthesis of 1,2-Amino Alcohols: TiCl3/t-BuOOH-Mediated Radical Hydroxymethylation of Imines," Organic Letters, 10(21):5063-5066 (2008).
Friedli, A., et al., "A convenient synthetic entry into aldehydes with extended conjugation," Tetrahedron, 53(8):2717-2730 (1997).
Friedli, A., et al., "A convenient synthetic entry into aldehydes with extended conjugation," Tetrahedron, 53(18):6233-6234 (1997).
Guo, C., et al., "Synthesis of new aromatic aldehydes bearing nitrogen mustard derivatives and haloalkylpiperazinyl," Youji Huaxue, 25(3):308-312 (2005).
International Search Report and Written Opinion for International Application No. PCT/US2018/041758, 11 pages (dated Sep. 28, 2018).
Li, F., et al., "Synthesis of γ-N-arylideneaminopropyl-2-methyl-6-phenyl-1,3-dioxa-6-aza-2-silacyclooctanes," Synthetic Communications, 31(23):3715-3720 (2001).
Ma, H., et al., "A novel synthesis of side-chain electro-optic polyimides with high azo chromophore density," European Polymer Journal, 34(8):1125-1132 (1998).
Massin, J., et al., "Near-Infrared Solid-State Emitters Based on Isophorone: Synthesis, Crystal Structure and Spectroscopic Properties," Chemistry of Materials, 23(3):862-873 (2011).
Nishiyama, T., et al., "Synthesis and NMR spectra of 6-phenyl-5,6,7,8-tetrahydro-4H-1,3,6-dioxazocines," Journal of Heterocyclic Chemistry, 23(1):69-71 (1986).
Shen, S., et al., "Mechanistic study of the oxidation of N-phenyldiethanolamine by bis(hydrogen periodato)argentate(III) complex anion," Transition Metal Chemistry, 32(2):167-171 (2007).
"Sul-free H2S & Acid Gas Eliminator," 6 pages, undated, but to the best of undersigned attorney's belief and knowledge is believed to be prior to the filing date of this application.
Yin, D., et al., "Synthesis of a novel organic nonlinear optical molecule MC-FTC," Huaxue Xuebao, 62(5):518-522 (2004).

(56) References Cited

OTHER PUBLICATIONS

Zhao, Y., et al., "A highly selective colorimetric chemodosimeter for fast and quantitative detection of hydrogen sulfide," Analyst (Cambridge, United Kingdom), 137(23):5576-5580 (2012).

Zhou, L., et al., "NLO Polymers Containing Anionic Chromophore," Journal of Macromolecular Science, Part A: Pure and Applied Chemistry, A42(10):1423-1434 (2005).

Zhou, L., et al., "Novel crosslinked nonlinear optical materials based on cellulose diacetate," Journal of Applied Polymer Science, 100(4):2832-2837 (2006).

* cited by examiner

HYDROGEN SULFIDE SCAVENGERS

TECHNICAL FIELD

The present disclosure relates generally to scavengers of sulfur-based species, and more particularly to alkanolamine formaldehyde compounds and compositions as scavengers of hydrogen sulfide and/or mercaptans.

BACKGROUND

The removal of sulfur-based species from liquid or gaseous hydrocarbon streams is a problem that has long challenged many industries. Hydrogen sulfide is a huge problem in the oil industry, particularly in the drilling, production, transportation, storage, and processing of crude oil, as well as waste water associated with crude oil. The same problems exist in the natural gas industry.

The presence of sulfur-containing compounds such as hydrogen sulfide can result in the deposition of sulfur containing salts, which can cause plugging and corrosion of transmission pipes, valves, regulators and other process equipment. Even flared natural gas needs to be treated to avoid acid rain generation due to $SO_x$ formation. Also, in the manufactured gas industry or coke making industry, coal-gas emissions containing unacceptable levels of hydrogen sulfide are commonly produced from destructive distillation of bituminous coal.

Since hydrogen sulfide has an offensive odor and natural gas containing it is called "sour" gas, treatments to lower hydrogen sulfide are termed "sweetening" processes. When a particular compound is used to remove or lower $H_2S$, it is called scavenging agent.

Despite the availability of scavengers for use in the oil and gas industry, there still exists a need for improved compounds, compositions and methods for removing sulfur-based species from liquid and gas streams.

SUMMARY

In one aspect, disclosed are scavenging compounds having formula (I),

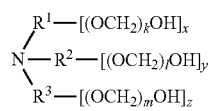

wherein $R^1$, $R^2$, and $R^3$ are each independently selected from the group consisting of hydrogen, alkylenyl, alkenylenyl, alkynylenyl, alkyl, alkenyl, and alkynyl, wherein said alkylenyl, alkenylenyl, alkynylenyl, alkyl, alkenyl, and alkynyl are each independently, at each occurrence, substituted or unsubstituted with one or more suitable substituents;

k, l, and m are each independently an integer selected from the group consisting of 0 to 25, wherein k+l+m is >0; and x, y, and z are each independently an integer selected from the group consisting of 0 and 1, wherein x+y+z is 1, 2, or 3; provided that:

when x is 0, $R^1$ is hydrogen, alkyl, alkenyl, or alkynyl; and when x is 1, $R^1$ is alkylenyl, alkenylenyl, or alkynylenyl;

when y is 0, $R^2$ is hydrogen, alkyl, alkenyl, or alkynyl; and when y is 1, $R^2$ is alkylenyl, alkenylenyl, or alkynylenyl;

when z is 0, $R^3$ is hydrogen, alkyl, alkenyl, or alkynyl; and when z is 1, $R^3$ is alkylenyl, alkenylenyl, or alkynylenyl.

In certain embodiments, when x is 1, y is 1, z is 1, k is 1, l is 1, and m is 1, then $R^1$, $R^2$, and $R^3$ are not simultaneously unsubstituted $C_2$-alkylenyl.

In certain embodiments, x+y+z is 3, and $R^1$, $R^2$, and $R^3$ are each alkylenyl. In certain embodiments, x+y+z is 3, and $R^1$, $R^2$, and $R^3$ are each $C_2$-alkylenyl. In certain embodiments, x+y+z is 3, and $R^1$, $R^2$, and $R^3$ are each unsubstituted $C_2$-alkylenyl. In certain embodiments, x is 1, y is 1, z is 0, $R^1$ and $R^2$ are each alkylenyl, and $R^3$ is alkyl. In certain embodiments, x is 1, y is 1, z is 0, $R^1$ and $R^2$ are each $C_2$-alkylenyl, and $R^3$ is $C_1$-alkyl. In certain embodiments, x is 1, y is 1, z is 0, $R^1$ and $R^2$ are each unsubstituted $C_2$-alkylenyl, and $R^3$ is unsubstituted $C_1$-alkyl. In certain embodiments, x is 1, y is 1, z is 0, $R^1$ and $R^2$ are each alkylenyl, and $R^3$ is hydrogen. In certain embodiments, x is 1, y is 1, z is 0, $R^1$ and $R^2$ are each $C_2$-alkylenyl, and $R^3$ is hydrogen. In certain embodiments, x is 1, y is 1, z is 0, $R^1$ and $R^2$ are each unsubstituted $C_2$-alkylenyl, and $R^3$ is hydrogen.

In another aspect, disclosed are scavenging compounds having formula (II),

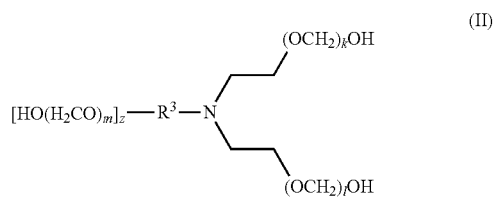

wherein $R^3$ is selected from the group consisting of hydrogen, alkylenyl, alkenylenyl, alkynylenyl, alkyl, alkenyl, and alkynyl, wherein said alkylenyl, alkenylenyl, alkynylenyl, alkyl, alkenyl, and alkynyl are each independently substituted or unsubstituted with one or more suitable substituents;

k, l, and m are each independently an integer selected from the group consisting of 1 to 25, wherein k+l+m>0; and z is 0 or 1;

provided that:

when z is 1, $R^3$ is alkylenyl, alkenylenyl, or alkynylenyl;

when z is 0, $R^3$ is hydrogen, alkyl, alkenyl, or alkynyl.

In certain embodiments, when z is 1, k is 1, l is 1, and m is 1, then $R^3$ is not an unsubstituted $C_2$-alkylenyl.

In another aspect, disclosed are scavenging compositions. In certain embodiments, the composition comprises a mixture of compounds of formula (I). In certain embodiments, the composition comprises mixture of compounds of formula (II).

In certain embodiments, the composition comprises one or more additives independently selected from the group consisting of asphaltene inhibitors, paraffin inhibitors, corrosion inhibitors, scale inhibitors, emulsifiers, water clarifiers, dispersants, emulsion breakers, hydrogen sulfide scavengers, gas hydrate inhibitors, biocides, pH modifiers, surfactants, solvents, and combinations thereof.

In certain embodiments, the composition comprises at least one surfactant or dispersant. In certain embodiments, the surfactant or dispersant may be a compound selected from the group consisting of alkyl benzyl ammonium chloride, benzyl cocoalkyl($C_{12}$-$C_{18}$)dimethylammonium chloride, dicocoalkyl($C_{12}$-$C_{18}$)dimethylammonium chloride, ditallow dimethylammonium chloride, di(hydrogenated tallow alkyl)dimethyl quaternary ammonium methyl chloride, methyl bis(2-hydroxyethyl cocoalkyl($C_{12}$-$C_{18}$) quaternary ammonium chloride, dimethyl(2-ethyl) tallow ammonium methyl sulfate, n-dodecylbenzyldimethylammonium chloride, n-octadecylbenzyldimethyl ammonium chloride, n-dodecyltrimethylammonium sulfate, soya alkyltrimethylammonium chloride, hydrogenated tallow alkyl (2-ethylhyexyl) dimethyl quaternary ammonium methyl sulfate, and combinations thereof.

In certain embodiments, the composition comprises at least one solvent. In certain embodiments, the solvent is water, a polyhydroxylated solvent, a polyether, an alcohol, or a combination thereof.

In another aspect, disclosed are methods of sweetening a fluid or gas. The method includes treating the fluid or gas with an effective amount of a compound of formula (I),

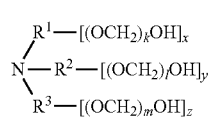
(I)

wherein $R^1$, $R^2$, and $R^3$ are each independently selected from the group consisting of hydrogen, alkylenyl, alkenylenyl, alkynylenyl, alkyl, alkenyl, and alkynyl, wherein said alkylenyl, alkenylenyl, alkynylenyl, alkyl, alkenyl, and alkynyl are each independently, at each occurrence, substituted or unsubstituted with one or more suitable substituents;

k, l, and m are each independently an integer selected from the group consisting of 0 to 25, wherein k+l+m>0; and x, y, and z are each independently an integer selected from the group consisting of 0 and 1, wherein x+y+z is 1, 2, or 3;

provided that:
when x is 0, $R^1$ is hydrogen, alkyl, alkenyl, or alkynyl; and
when x is 1, $R^1$ is alkylenyl, alkenylenyl, or alkynylenyl;
when y is 0, $R^2$ is hydrogen, alkyl, alkenyl, or alkynyl; and
when y is 1, $R^2$ is alkylenyl, alkenylenyl, or alkynylenyl;
when z is 0, $R^3$ is hydrogen, alkyl, alkenyl, or alkynyl; and
when z is 1, $R^3$ is alkylenyl, alkenylenyl, or alkynylenyl.

In certain embodiments, the method includes use of a compound of formula (I) with the proviso that when x is 1, y is 1, z is 1, k is 1, l is 1, and m is 1, then $R^1$, $R^2$, and $R^3$ are not simultaneously unsubstituted $C_2$-alkylenyl.

In certain embodiments, the method includes use of a compound of formula (I) wherein x+y+z is 3, and $R^1$, $R^2$, and $R^3$ are each alkylenyl. In certain embodiments, the method includes use of a compound of formula (I) wherein x+y+z is 3, and $R^1$, $R^2$, and $R^3$ are each $C_2$-alkylenyl. In certain embodiments, the method includes use of a compound of formula (I) wherein x+y+z is 3, and $R^1$, $R^2$, and $R^3$ are each unsubstituted $C_2$-alkylenyl. In certain embodiments, the method includes use of a compound of formula (I) wherein x is 1, y is 1, z is 0, $R^1$ and $R^2$ are each alkylenyl, and $R^3$ is alkyl. In certain embodiments, the method includes use of a compound of formula (I) wherein x is 1, y is 1, z is 0, $R^1$ and $R^2$ are each $C_2$-alkylenyl, and $R^3$ is $C_1$-alkyl. In certain embodiments, the method includes use of a compound of formula (I) wherein x is 1, y is 1, z is 0, $R^1$ and $R^2$ are each unsubstituted $C_2$-alkylenyl, and $R^3$ is unsubstituted $C_1$-alkyl. In certain embodiments, the method includes use of a compound of formula (I) wherein x is 1, y is 1, z is 0, $R^1$ and $R^2$ are each alkylenyl, and $R^3$ is hydrogen. In certain embodiments, the method includes use of a compound of formula (I) wherein x is 1, y is 1, z is 0, $R^1$ and $R^2$ are each $C_2$-alkylenyl, and $R^3$ is hydrogen. In certain embodiments, the method includes use of a compound of formula (I) wherein x is 1, y is 1, z is 0, $R^1$ and $R^2$ are each unsubstituted $C_2$-alkylenyl, and $R^3$ is hydrogen.

In certain embodiments, the method includes use of a compound of formula (II),

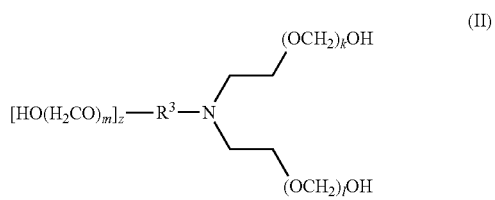
(II)

wherein $R^3$ is selected from the group consisting of hydrogen, alkylenyl, alkenylenyl, alkynylenyl, alkyl, alkenyl, and alkynyl, wherein said alkylenyl, alkenylenyl, alkynylenyl, alkyl, alkenyl, and alkynyl are each independently substituted or unsubstituted with one or more suitable substituents;

k, l, and m are each independently an integer selected from the group consisting of 0 to 25, wherein k+l+m>0; and z is 0 or 1;

provided that:
when z is 1, $R^3$ is alkylenyl, alkenylenyl, or alkynylenyl;
when z is 0, $R^3$ is hydrogen, alkyl, alkenyl, or alkynyl.

In certain embodiments, the method includes use of a compound of formula (II) with the proviso that when z is 1, k is 1, l is 1, and m is 1, then $R^3$ is not an unsubstituted $C_2$-alkylenyl.

In certain embodiments, the method includes treating the fluid or gas with an effective amount of a composition comprising one or more compounds of formula (I). In certain embodiments, the method includes treating the fluid or gas with an effective amount of a composition comprising one or more compounds of formula (II). In certain embodiments, the composition further comprises one or more additional components, each component independently selected from the group consisting of asphaltene inhibitors, paraffin inhibitors, corrosion inhibitors, scale inhibitors, emulsifiers, water clarifiers, dispersants, emulsion breakers, hydrogen sulfide scavengers, gas hydrate inhibitors, biocides, pH modifiers, surfactants, solvents, and combinations thereof.

In certain embodiments, the composition comprises at least one surfactant or dispersant. In certain embodiments, the surfactant or dispersant may be a compound selected from the group consisting of alkyl benzyl ammonium chloride, benzyl cocoalkyl($C_{12}$-$C_{18}$)dimethylammonium chloride, dicocoalkyl($C_{12}$-$C_{18}$)dimethylammonium chloride, ditallow dimethylammonium chloride, di(hydrogenated tallow alkyl)dimethyl quaternary ammonium methyl chloride, methyl bis(2-hydroxyethyl cocoalkyl($C_{12}$-$C_{18}$) quaternary ammonium chloride, dimethyl(2-ethyl) tallow ammonium methyl sulfate, n-dodecylbenzyldimethylammonium chloride, n-octadecylbenzyldimethyl ammonium chloride, n-dodecyltrimethylammonium sulfate, soya alkyltrimethylammonium chloride, hydrogenated tallow alkyl (2-ethylhyexyl) dimethyl quaternary ammonium methyl sulfate, and combinations thereof.

In certain embodiments, the composition comprises at least one solvent. In certain embodiments, the solvent is water, a polyhydroxylated solvent, a polyether, an alcohol, or a combination thereof.

In certain embodiments, the method reduces hydrogen sulfide in the treated fluid or gas by at least 99%.

In certain embodiments, the method includes applying a compound of formula (I), or composition comprising a compound of formula (I), to a gas or liquid produced or used in the production, transportation, storage, and/or separation of crude oil and natural gas. In certain embodiments, the method includes applying a compound of formula (I), or composition comprising a compound of formula (I), to a gas stream used or produced in a coal-fired process, such as a coal-fired power plant. In certain embodiments, the method includes applying a compound of formula (I), or composition comprising a compound of formula (I), to a gas or liquid produced or used in a waste-water process, a farm, a slaughter house, a land-fill, a municipality waste-water plant, a coking coal process, or a biofuel process.

In another aspect, disclosed are processes for preparing compounds of formula (I). In certain embodiments, a process for preparing a compound of formula (I) includes treating an amine of formula (1) with an aldehyde of formula (2),

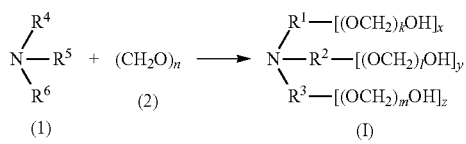

wherein, $R^4$, $R^5$, and $R^6$ of formula (1) are each independently selected from hydrogen, alkyl, alkenyl, and alkynyl, provided that at least one of $R^4$, $R^5$, and $R^6$ includes at least one hydroxyl group available for reaction with the compound of formula (2); and n ranges from 1 to 100.

The compounds, compositions, methods and processes are further described herein.

DETAILED DESCRIPTION

Disclosed herein are hydrogen sulfide and/or mercaptan scavenging compounds and compositions, methods of using said compounds and compositions, and processes for their preparation. The compounds and compositions are particularly useful in the control of hydrogen sulfide and/or mercaptan emissions from crude oil based, natural gas based, and coal based products and processes. The compounds and compositions are applicable to both upstream and downstream processes. The scavenging compounds and compositions, optionally blended with aqueous and/or non-aqueous solvents, are useful in a wide range of climates and under a wide range of process conditions.

The disclosed processes for preparing the compounds and compositions of the invention are economic, waste free, and provide said compounds in quantitative yields. In certain embodiments, the compounds and compositions may be obtained in anhydrous form, thereby providing use in processes where it is desirable to minimize water content (e.g., in an oil production process). Producing the compounds and compositions in anhydrous form also allows for reduced transportation costs. The anhydrous compounds and compositions can optionally be blended with hydrophilic solvents (e.g., alcohols, glycol, polyols) for non-aqueous applications. Alternatively, the compounds and compositions may be blended with an aqueous phase for direct use in aqueous applications.

The compounds and compositions of the invention provide further economic advantages through reduced transportation costs due to increased actives concentration, and through increased production capacity. The compounds and compositions of the invention also considerably lower the water washable nitrogen content to eliminate nitrogen contamination of refinery catalyst beds. The compounds and compositions also provide the ability to manufacture the products at most locations without offensive odor emanating from raw materials.

1. DEFINITION OF TERMS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "suitable substituent," as used herein, is intended to mean a chemically acceptable functional group, preferably a moiety that does not negate the hydrogen sulfide scavenging activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, groups of formula —(OCH$_2$)$_t$OH wherein t is 1 to 25, and groups of formula -alkylenyl-(OCH$_2$)$_t$OH wherein t is 1 to 25. Those skilled in the art will appreciate that many substituents can be substituted by additional substituents.

The term "alkyl," as used herein, refers to a linear or branched hydrocarbon radical, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Alkyl groups include, but are not limited to, methyl, ethyl, n-propyl, isopropyl, n-butyl, iso-butyl, secondary-butyl, and tertiary-butyl. Alkyl groups may be unsubstituted or substituted by one or more suitable substituents, as defined above.

The term "alkylenyl" or "alkylene," as used herein, refers to a divalent group derived from a saturated, straight or branched hydrocarbon chain of from 1 to 32 carbon atoms. The term "$C_1$-$C_6$ alkylene" means those alkylene or alkylenyl groups having from 1 to 6 carbon atoms. Representative examples of alkylenyl groups include, but are not limited to, —$CH_2$—, —$CH(CH_3)$—, —$CH(C_2H_5)$—, —$CH(CH(CH_3)(C_2H_5))$—, —$C(H)(CH_3)CH_2CH_2$—, —$C(CH_3)_2$—, —$CH_2CH_2$—, —$CH_2CH_2CH_2$—, —$CH_2CH_2CH_2CH_2$—, and —$CH_2CH(CH_3)CH_2$—. Alkylenyl groups may be unsubstituted or substituted by one or more suitable substituents, as defined above.

The term "alkenyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined above.

The term "alkenylenyl" or "alkenylene," as used herein, refers to a divalent group derived from a straight or branched chain hydrocarbon of 2 to 32 carbon atoms, which contains at least one carbon-carbon double bond. Representative examples of alkenylenyl groups include, but are not limited to, —$C(H)=C(H)$—, —$C(H)=C(H)$—$CH_2$—, —$C(H)=C(H)$—$CH_2$—$CH_2$—, —$CH_2$—$C(H)=C(H)$—$CH_2$—, —$C(H)=C(H)$—$CH(CH_3)$—, and —$CH_2$—$C(H)=C(H)$—$CH(CH_2CH_3)$—. Alkenylenyl groups may be unsubstituted or substituted by one or more suitable substituents, as defined above.

The term "alkynyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon triple bonds. Alkynyl groups include, but are not limited to, ethynyl, propynyl, and butynyl. Alkynyl groups may be unsubstituted or substituted by one or more suitable substituents, as defined above.

The term "alkynylenyl" or "alkynylene," as used herein, refers to a divalent unsaturated hydrocarbon group which may be linear or branched and which has at least one carbon-carbon triple bond. Representative examples of alkynylenyl groups include, but are not limited to, —C≡C—, —C≡C—$CH_2$—, —C≡C—$CH_2$—$CH_2$—, —$CH_2$—C≡C—$CH_2$—, —C≡C—$CH(CH_3)$—, and —$CH_2$—C≡C—$CH(CH_2CH_3)$—. Alkynylenyl groups may be unsubstituted or substituted by one or more suitable substituents, as defined above.

The term "alkoxy," as used herein, refers to an alkyl group, as defined herein, appended to the parent molecular moiety through an oxygen atom.

The term "aryl," as used herein, means monocyclic, bicyclic, or tricyclic aromatic radicals such as phenyl, naphthyl, tetrahydronaphthyl, indanyl and the like; optionally substituted by one or more suitable substituents, preferably 1 to 5 suitable substituents, as defined above.

The term "carbonyl," "(C=O)," or "—C(O)—" (as used in phrases such as alkylcarbonyl, alkyl —(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

The term "cycloalkyl," as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups may be unsubstituted or substituted by one or more suitable substituents, preferably 1 to 5 suitable substituents, as defined above.

The term "halo" or "halogen," as used herein, refers to a fluoro, chloro, bromo or iodo radical.

The term "heteroaryl," as used herein, refers to a monocyclic, bicyclic, or tricyclic aromatic heterocyclic group containing one or more heteroatoms selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups may be unsubstituted or substituted by one or more suitable substituents, preferably 1 to 5 suitable substituents, as defined above.

The term "heterocycle," as used herein, refers to a monocyclic, bicyclic, or tricyclic group containing 1 to 4 heteroatoms selected from N, O, $S(O)_n$, $P(O)_n$, $PR^x$, NH or $NR^x$, wherein $R^x$ is a suitable substituent. Heterocyclic groups optionally contain 1 or 2 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, preferably 1 to 3 suitable substituents, as defined above.

The term "hydroxy," as used herein, refers to an —OH group.

The term "oxo," as used herein, refers to a double bonded oxygen (=O) radical wherein the bond partner is a carbon atom. Such a radical can also be thought as a carbonyl group.

The term "counterion," as used herein, means a halide (e.g., fluoride, chloride, bromide, iodide), a carboxylate anion, such as selected from deprotonation of mineral acid, acrylic acid, acetic acid, methacrylic acid, glycolic acid, thioglycolic acid, propionic acid, butyric acid, and the like, or any other anionic constituent that satisfies the charge balance necessary to form a neutral molecule.

The term "sweetening," as used herein, may refer to a process that removes sulfur species from a gas or liquid. The sulfur species may include hydrogen sulfide and mercaptans.

The term "sour gas," as used herein, may refer to a gas that includes significant amounts of sulfur species, such as hydrogen sulfide and/or mercaptans.

The term "sour liquid" or "sour fluid," as used herein, may refer to a liquid that includes significant amounts of sulfur species, such as hydrogen sulfide and/or mercaptans.

The term "water cut," as used herein, means the percentage of water in a composition containing an oil and water mixture.

2. COMPOUNDS

Compounds of the invention include scavengers of sulfur-based species, such as hydrogen sulfide and mercaptans. The compounds may be particularly useful in the oil, gas, and coal industries. The compounds may be alkanolamine formaldehyde addition products. The alkanolamine formaldehyde addition products may be provided in anhydrous or hydrous form.

In one aspect, compounds of the invention have formula (I),

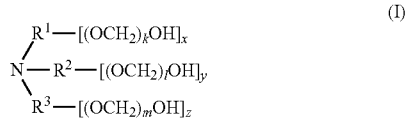

wherein, $R^1$, $R^2$, and $R^3$ are each independently selected from the group consisting of hydrogen, alkylenyl, alkenylenyl, alkynylenyl, alkyl, alkenyl, and alkynyl, wherein said alkylenyl, alkenylenyl, alkynylenyl, alkyl, alkenyl, and alkynyl are each independently, at each occurrence, substituted or unsubstituted with one or more suitable substituents;

k, l, and m are each independently an integer selected from the group consisting of 0 to 25, wherein k+l+m is >0; and x, y, and z are each independently an integer selected from the group consisting of 0 and 1, wherein x+y+z is 1, 2, or 3;
provided that:
when x is 0, $R^1$ is hydrogen, alkyl, alkenyl, or alkynyl; and
when x is 1, $R^1$ is alkylenyl, alkenylenyl, or alkynylenyl;
when y is 0, $R^2$ is hydrogen, alkyl, alkenyl, or alkynyl; and
when y is 1, $R^2$ is alkylenyl, alkenylenyl, or alkynylenyl;
when z is 0, $R^3$ is hydrogen, alkyl, alkenyl, or alkynyl; and
when z is 1, $R^3$ is alkylenyl, alkenylenyl, or alkynylenyl.

It is to be understood that when x is 0, $[(OCH_2)_kOH]$ is absent; when y is 0, $[(OCH_2)_lOH]$ is absent; and when z is 0, $[(OCH_2)_mOH]$ is absent. It is also to be understood that when $R^1$ is alkylenyl, alkenylenyl, or alkynylenyl, then x must be 1; when $R^1$ is hydrogen, alkyl, alkenyl, or alkynyl, then x must be 0; when $R^2$ is alkylenyl, alkenylenyl, or alkynylenyl, then y must be 1; when $R^2$ is hydrogen, alkyl, alkenyl, or alkynyl, then y must be 0; when $R^3$ is alkylenyl, alkenylenyl, or alkynylenyl, then z must be 1; and when $R^3$ is hydrogen, alkyl, alkenyl, or alkynyl, then z must be 0.

It is also to be understood that when k>0, then x must be 1; when l>0, then y must be 1; and when m is >0, then z must be 1.

In certain embodiments, one or more of $R^1$, $R^2$, and $R^3$ are straight chain alkylenyl. In certain embodiments, one or more of $R^1$, $R^2$, and $R^3$ are branched alkylenyl. In certain embodiments, one or more of $R^1$, $R^2$, and $R^3$ are unsubstituted alkylenyl. In certain embodiments, one or more of $R^1$, $R^2$, and $R^3$ are substituted alkylenyl. In certain embodiments, one or more of $R^1$, $R^2$, and $R^3$ are straight chain, unsubstituted alkylenyl. In certain embodiments, one or more of $R^1$, $R^2$, and $R^3$ are straight chain, substituted alkylenyl. In certain embodiments, one or more of $R^1$, $R^2$, and $R^3$ are branched, unsubstituted alkylenyl. In certain embodiments, one or more of $R^1$, $R^2$, and $R^3$ are branched, substituted alkylenyl.

In certain embodiments, $R^1$, $R^2$, and $R^3$ are each straight chain alkylenyl. In certain embodiments, $R^1$, $R^2$, and $R^3$ are each branched alkylenyl. In certain embodiments, $R^1$, $R^2$, and $R^3$ are each unsubstituted alkylenyl. In certain embodiments, $R^1$, $R^2$, and $R^3$ are each substituted alkylenyl. In certain embodiments, $R^1$, $R^2$, and $R^3$ are each straight chain, unsubstituted alkylenyl. In certain embodiments, $R^1$, $R^2$, and $R^3$ are each straight chain, substituted alkylenyl. In certain embodiments, $R^1$, $R^2$, and $R^3$ are each branched, unsubstituted alkylenyl. In certain embodiments, $R^1$, $R^2$, and $R^3$ are each branched, substituted alkylenyl.

In certain embodiments, $R^1$, $R^2$, and $R^3$ are each $C_1$-$C_{32}$-alkylenyl. In certain embodiments, $R^1$, $R^2$, and $R^3$ are each $C_1$-$C_{24}$-alkylenyl. In certain embodiments, $R^1$, $R^2$, and $R^3$ are each $C_1$-$C_{10}$ alkylenyl. In certain embodiments, $R^1$, $R^2$, and $R^3$ are each $C_1$-$C_6$-alkylenyl.

In certain embodiments, one or more of $R^1$, $R^2$, and $R^3$ are $C_1$-alkylenyl. In certain embodiments, one or more of $R^1$, $R^2$, and $R^3$ are unsubstituted $C_1$-alkylenyl. In certain embodiments, one or more of $R^1$, $R^2$, and $R^3$ are substituted $C_1$-alkylenyl. In certain embodiments, one or more of $R^1$, $R^2$, and $R^3$ are $C_2$-alkylenyl. In certain embodiments, one or more of $R^1$, $R^2$, and $R^3$ are unsubstituted $C_2$-alkylenyl. In certain embodiments, one or more of $R^1$, $R^2$, and $R^3$ are substituted $C_2$-alkylenyl. In certain embodiments, one or more of $R^1$, $R^2$, and $R^3$ are $C_3$-alkylenyl. In certain embodiments, one or more of $R^1$, $R^2$, and $R^3$ are unsubstituted $C_3$-alkylenyl. In certain embodiments, one or more of $R^1$, $R^2$, and $R^3$ are substituted $C_3$-alkylenyl. In certain embodiments, one or more of $R^1$, $R^2$, and $R^3$ are $C_4$-alkylenyl. In certain embodiments, one or more of $R^1$, $R^2$, and $R^3$ are unsubstituted $C_4$-alkylenyl. In certain embodiments, one or more of $R^1$, $R^2$, and $R^3$ are substituted $C_4$-alkylenyl. In certain embodiments, one or more of $R^1$, $R^2$, and $R^3$ are $C_5$-alkylenyl. In certain embodiments, one or more of $R^1$, $R^2$, and $R^3$ are unsubstituted $C_5$-alkylenyl. In certain embodiments, one or more of $R^1$, $R^2$, and $R^3$ are substituted $C_5$-alkylenyl. In certain embodiments, one or more of $R^1$, $R^2$, and $R^3$ are $C_6$-alkylenyl. In certain embodiments, one or more of $R^1$, $R^2$, and $R^3$ are unsubstituted $C_6$-alkylenyl. In certain embodiments, one or more of $R^1$, $R^2$, and $R^3$ are substituted $C_6$-alkylenyl.

In certain embodiments, $R^1$, $R^2$, and $R^3$ are each $C_1$-alkylenyl. In certain embodiments, $R^1$, $R^2$, and $R^3$ are each unsubstituted $C_1$-alkylenyl. In certain embodiments, $R^1$, $R^2$, and $R^3$ are each substituted $C_1$-alkylenyl. In certain embodiments, $R^1$, $R^2$, and $R^3$ are each $C_2$-alkylenyl. In certain embodiments, $R^1$, $R^2$, and $R^3$ are each unsubstituted $C_2$-alkylenyl. In certain embodiments, $R^1$, $R^2$, and $R^3$ are each substituted $C_2$-alkylenyl. In certain embodiments, $R^1$, $R^2$, and $R^3$ are each $C_3$-alkylenyl. In certain embodiments, $R^1$, $R^2$, and $R^3$ are each unsubstituted $C_3$-alkylenyl. In certain embodiments, $R^1$, $R^2$, and $R^3$ are each substituted $C_3$-alkylenyl. In certain embodiments, $R^1$, $R^2$, and $R^3$ are each $C_4$-alkylenyl. In certain embodiments, $R^1$, $R^2$, and $R^3$ are each unsubstituted $C_4$-alkylenyl. In certain embodiments, $R^1$, $R^2$, and $R^3$ are each substituted $C_4$-alkylenyl. In certain embodiments, $R^1$, $R^2$, and $R^3$ are each $C_5$-alkylenyl. In certain embodiments, $R^1$, $R^2$, and $R^3$ are each unsubstituted $C_5$-alkylenyl. In certain embodiments, $R^1$, $R^2$, and $R^3$ are each substituted $C_5$-alkylenyl. In certain embodiments, $R^1$, $R^2$, and $R^3$ are each $C_6$-alkylenyl. In certain embodiments, $R^1$, $R^2$, and $R^3$ are each unsubstituted $C_6$-alkylenyl. In certain embodiments, $R^1$, $R^2$, and $R^3$ are each substituted $C_6$-alkylenyl.

In certain embodiments, when x is 1, y is 1, z is 1, k is 1, l is 1, and m is 1, then $R^1$, $R^2$, and $R^3$ are not simultaneously unsubstituted $C_2$-alkylenyl.

In certain embodiments, $R^1$ and $R^2$ are alkylenyl, and $R^3$ is alkyl. In certain embodiments, $R^1$ and $R^2$ are unsubstituted alkylenyl, and $R^3$ is unsubstituted alkyl. In certain embodiments, $R^1$ and $R^2$ are substituted alkylenyl, and $R^3$ is unsubstituted alkyl. In certain embodiments, $R^1$ and $R^2$ are substituted alkylenyl, and $R^3$ is substituted alkyl. In certain embodiments, $R^1$ and $R^2$ are unsubstituted alkylenyl, and $R^3$ is substituted alkyl.

In certain embodiments, $R^1$ and $R^2$ are $C_1$-$C_{32}$, $C_1$-$C_{16}$, $C_1$-$C_{10}$, or $C_1$-$C_6$ alkylenyl, and $R^3$ is $C_1$-$C_{32}$, $C_1$-$C_{16}$, $C_1$-$C_{10}$, or $C_1$-$C_6$ alkyl. In certain embodiments, $R^1$ and $R^2$ are unsubstituted $C_1$-$C_{32}$, $C_1$-$C_{16}$, $C_1$-$C_{10}$, or $C_1$-$C_6$ alkylenyl, and $R^3$ is unsubstituted $C_1$-$C_{32}$, $C_1$-$C_{16}$, $C_1$-$C_{10}$, or $C_1$-$C_6$ alkyl. In certain embodiments, $R^1$ and $R^2$ are unsubstituted $C_2$-alkylenyl, and $R^3$ is unsubstituted $C_1$-alkyl. In certain embodiments, $R^1$ and $R^2$ are unsubstituted $C_2$-alkylenyl, and $R^3$ is unsubstituted $C_2$-alkyl.

In certain embodiments, $R^1$ and $R^2$ are alkylenyl, and $R^3$ is hydrogen. In certain embodiments, $R^1$ and $R^2$ are unsubstituted alkylenyl, and $R^3$ is hydrogen. In certain embodiments, $R^1$ and $R^2$ are unsubstituted $C_2$-alkylenyl, and $R^3$ is hydrogen. In certain embodiments, $R^1$ and $R^2$ are substituted alkylenyl, and $R^3$ is hydrogen. In certain embodiments, $R^1$ and $R^2$ are substituted $C_2$-alkylenyl, and $R^3$ is hydrogen.

In certain embodiments, one or more of $R^1$, $R^2$, and $R^3$ are substituted with one or more suitable substituents selected from hydroxy, groups of formula —$(OCH_2)_tOH$ wherein t is 1 to 25, and groups of formula -alkylenyl-$(OCH_2)_tOH$ wherein t is 1 to 25.

In certain embodiments, k is 0 to 25, l is 0 to 25, and m is 0 to 25, provided that k+l+m is >0. In certain embodiments, k is 1 to 25, l is 1 to 25, and m is 1 to 25. In certain embodiments, k is 1 to 20, l is 1 to 20, and m is 1 to 20. In certain embodiments, k is 1 to 13, l is 1 to 13, and m is 1 to 13. In certain embodiments, k is 1 to 10, l is 1 to 10, and m is 1 to 10.

In certain embodiments, k+l+m ranges from 1 to 25. In certain embodiments, k+l+m ranges from 1 to 13. In certain embodiments, k+l+m ranges from 1 to 10. In certain embodiments, k+l+m is 1, 2, 3, 4, 5, 6, 7, 8, 9, 10, 11, 12, 13, 14, 15, 16, 17, 18, 19, 20, 21, 22, 23, 24, or 25.

In certain embodiments, x is 1, y is 1, and z is 1. In certain embodiments, x is 1, y is 1, and z is 0. In certain embodiments, x is 1, y is 0, and z is 1. In certain embodiments, x is 0, y is 1, and z is 1. In certain embodiments, x is 1, y is 0, and z is 0. In certain embodiments, x is 0, y is 1, and z is 0. In certain embodiments, x is 0, y is 0, and z is 1.

In certain embodiments, a compound of the invention has formula (II), wherein $R^3$ is selected from the group consisting of hydrogen, alkylenyl, alkenylenyl, alkynylenyl, alkyl, alkenyl, and alkynyl, wherein said alkylenyl, alkenylenyl, alkynylenyl, alkyl, alkenyl, and alkynyl are each independently substituted or unsubstituted with one or more suitable substituents; wherein k, l, and m are each independently an integer selected from the group consisting of 0 to 25, wherein k+l+m>0; and wherein z is 0 or 1; provided that when z is 1, $R^3$ is alkylenyl, alkenylenyl, or alkynylenyl; provided that when z is 0, $R^3$ is hydrogen, alkyl, alkenyl, or alkynyl.

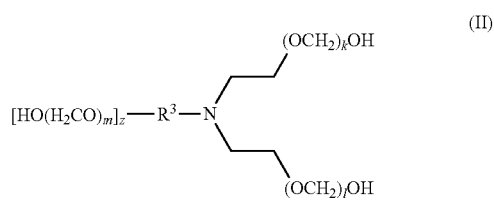

(II)

It is to be understood that when z is 0, $[HO(H_2CO)_m]$ is absent. It is also understood that when m is >0, then z must be 1. In certain embodiments, when z is 1, k is 1, and l is 1, then $R^3$ is not an unsubstituted $C_2$-alkylenyl. In certain embodiments, z is 1 and $R^3$ is alkylenyl. In certain embodiments, z is 1 and $R^3$ is $C_2$-alkylenyl. In certain embodiments, z is 1 and $R^3$ is unsubstituted $C_2$-alkylenyl. In certain embodiments, z is 0 and $R^3$ is alkyl. In certain embodiments, z is 0 and $R^3$ is $C_1$-alkyl. In certain embodiments, z is 0 and $R^3$ is unsubstituted $C_1$-alkyl. In certain embodiments, z is 0 and $R^3$ is hydrogen. In certain embodiments, k is 0 to 25, l is 0 to 25, and m is 0 to 25. In certain embodiments, k is 1 to 25, l is 1 to 25, and m is 1 to 25. In certain embodiments, k is 1 to 20, l is 1 to 20, and m is 1 to 20. In certain embodiments, k is 1 to 13, l is 1 to 13, and m is 1 to 13. In certain embodiments, k is 1 to 10, l is 1 to 10, and m is 1 to 10. In certain embodiments, k+l+m ranges from 1 to 25. In certain embodiments, k+l+m ranges from 1 to 13. In certain embodiments, k+l+m ranges from 1 to 10. In certain embodiments, k+l+m is 1, 2, 3, 4, 5, 6, 7, 8, 9, 10, 11, 12, 13, 14, 15, 16, 17, 18, 19, 20, 21, 22, 23, 24, or 25. In certain embodiments, when z is 1, k is 1, l is 1, and m is 1, then $R^3$ is not an unsubstituted $C_2$-alkylenyl.

In certain embodiments, a compound of the invention has formula (III), wherein k is 0 to 25, l is 0 to 25, and m is 0 to 25, provided that k+l+m is >0. In certain embodiments, k is 1 to 25, l is 1 to 25, and m is 1 to 25. In certain embodiments, k is 1 to 20, l is 1 to 20, and m is 1 to 20. In certain embodiments, k is 1 to 13, l is 1 to 13, and m is 1 to 13. In certain embodiments, k is 1 to 10, l is 1 to 10, and m is 1 to 10. In certain embodiments, k+l+m ranges from 1 to 25. In certain embodiments, k+l+m ranges from 1 to 13. In certain embodiments, k+l+m ranges from 1 to 10. In certain embodiments, k+l+m is 1, 2, 3, 4, 5, 6, 7, 8, 9, 10, 11, 12, 13, 14, 15, 16, 17, 18, 19, 20, 21, 22, 23, 24, or 25. In certain embodiments, k, l, and m are not simultaneously 1.

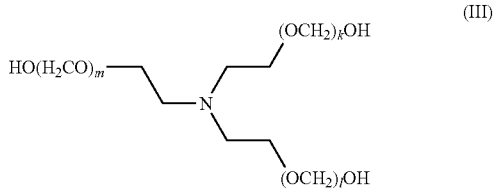

(III)

In certain embodiments, a compound of the invention has formula (IV), wherein $R^3$ is hydrogen, alkyl, alkenyl, or alkynyl, wherein said alkyl, alkenyl, and alkynyl are each independently substituted or unsubstituted with one or more suitable substituents, and wherein k and l are each independently an integer selected from the group consisting of 0 to 25, provided that k+l is >0. In certain embodiments, $R^3$ is alkyl. In certain embodiments, $R^3$ is unsubstituted $C_1$-alkyl or unsubstituted $C_2$-alkyl. In certain embodiments, $R^3$ is hydrogen. In certain embodiments, k is 1 to 25, and l is 1 to 25. In certain embodiments, k is 1 to 20, and l is 1 to 20. In certain embodiments, k is 1 to 13, and l is 1 to 13. In certain embodiments, k is 1 to 10, and l is 1 to 10. In certain embodiments, k+l ranges from 1 to 25. In certain embodiments, k+l ranges from 1 to 13. In certain embodiments, k+l ranges from 1 to 10. In certain embodiments, k+l is 1, 2, 3, 4, 5, 6, 7, 8, 9, 10, 11, 12, 13, 14, 15, 16, 17, 18, 19, 20, 21, 22, 23, 24, or 25.

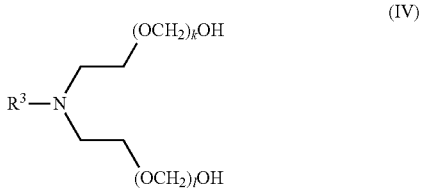

(IV)

In certain embodiments, a compound of the invention has formula (V), wherein k and l are each independently an integer selected from the group consisting of 0 to 25, provided that k+l is >0. In certain embodiments, k is 1 to 25, and l is 1 to 25. In certain embodiments, k is 1 to 20, and l is 1 to 20. In certain embodiments, k is 1 to 13, and l is 1 to 13. In certain embodiments, k is 1 to 10, and l is 1 to 10. In certain embodiments, k+l ranges from 1 to 25. In certain embodiments, k+l ranges from 1 to 13. In certain embodiments, k+l ranges from 1 to 10. In certain embodiments, k+l is 1, 2, 3, 4, 5, 6, 7, 8, 9, 10, 11, 12, 13, 14, 15, 16, 17, 18, 19, 20, 21, 22, 23, 24, or 25.

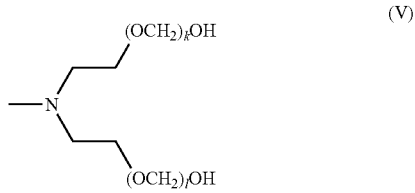

(V)

In certain embodiments, a compound of the invention has formula (VI), wherein k and l are each independently an integer selected from the group consisting of 0 to 25, provided that k+l is >0. In certain embodiments, k is 1 to 25, and l is 1 to 25. In certain embodiments, k is 1 to 20, and l is 1 to 20. In certain embodiments, k is 1 to 13, and l is 1 to 13. In certain embodiments, k is 1 to 10, and l is 1 to 10. In certain embodiments, k+l ranges from 1 to 25. In certain embodiments, k+l ranges from 1 to 13. In certain embodiments, k+l ranges from 1 to 10. In certain embodiments, k+l is 1, 2, 3, 4, 5, 6, 7, 8, 9, 10, 11, 12, 13, 14, 15, 16, 17, 18, 19, 20, 21, 22, 23, 24, or 25.

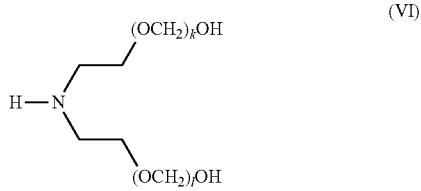

(VI)

In certain embodiments, a compound of the invention has formula (VII), wherein $R^3$, m, and z are as defined above.

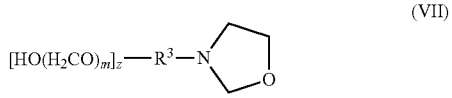

(VII)

The compounds of the invention may contain asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds.

3. COMPOSITIONS

The compositions disclosed herein include at least one compound as described above. In certain embodiments, a composition of the invention contains a pure composition of a compound of formula (I). In other embodiments, a composition of the invention contains a mixture of two or more structurally distinct compounds of formula (I). In certain embodiments, a composition of the invention may comprise a mixture of compounds of formula (I), wherein k, l, and/or m are variable, and/or wherein $R^1$, $R^2$, and/or $R^3$ are variable, and/or wherein x, y, and/or z are variable.

In certain embodiments, a composition of the invention contains a mixture of compounds of formula (I) wherein $R^1$, $R^2$, and $R^3$ are the same across the compounds of formula (I) in the composition, respectively, and k, l, and m are optionally variable across the compounds of formula (I) in the composition, respectively. For example, in certain embodiments, a composition of the invention may include a mixture of compounds of formula (I), wherein $R^1$, $R^2$, and $R^3$ are each unsubstituted $C_2$-alkylenyl; k, l, and m are each independently an integer selected from the group consisting of 1 to 25; and x, y, and z are each 1. In certain embodiments, a composition of the invention may include a mixture of compounds of formula (I), wherein $R^1$ and $R^2$ are each unsubstituted $C_2$-alkylenyl, and $R^3$ is methyl; k and l are each independently an integer selected from the group consisting of 1 to 25, and m is absent; and x and y are 1, and z is 0. In certain embodiments, a composition of the invention may include a mixture of compounds of formula (I), wherein $R^1$ and $R^2$ are each unsubstituted $C_2$-alkylenyl, and $R^3$ is hydrogen; k and l are each independently an integer selected from the group consisting of 1 to 25, and m is absent; and x and y are 1, and z is 0.

In certain embodiments, a composition of the invention contains a pure composition of a compound of formula (II), a pure composition of a compound of formula (III), a pure composition of a compound of formula (IV), a pure composition of a compound of formula (V), a pure composition of a compound of formula (VI), or any combination thereof, wherein the variables of said formulas are as defined above.

In certain embodiments, a composition of the invention contains a mixture of compounds of formula (II), a mixture of compounds of formula (III), a mixture of compounds of formula (IV), a mixture of compounds of formula (V), a mixture of compounds of formula (VI), or any combination thereof, wherein the variables of said formulas are as defined above.

In certain embodiments, a composition of the invention comprises from about 20 to about 100 percent by weight of one or more compounds of the invention, or from about 20 to about 98 percent by weight of one or more compounds of the invention, or from about 50 to 97 percent by weight of one or more compounds of the invention.

The compositions of the invention can optionally include one or more additives. Suitable additives include, but are not limited to, asphaltene inhibitors, paraffin inhibitors, corrosion inhibitors, scale inhibitors, emulsifiers, water clarifiers, dispersants, emulsion breakers, hydrogen sulfide scavengers, gas hydrate inhibitors, biocides, pH modifiers, surfactants, solvents, and combinations thereof.

a. Asphaltene Inhibitors

Suitable asphaltene inhibitors include, but are not limited to, aliphatic sulphonic acids; alkyl aryl sulphonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, polyisobutylene succinic anhydride, and combinations thereof.

b. Paraffin Inhibitors

Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes, and combinations thereof. Suitable dispersants include, but are not limited to, dodecyl benzene sulfonate, oxyalkylated alkylphenols, oxyalkylated alkylpnenolic resins, and combinations thereof.

c. Corrosion Inhibitors

Suitable corrosion inhibitors include, but are not limited to, amidoamines, quaternary amines, amides, phosphate esters, and combinations thereof.

d. Scale Inhibitors

Suitable scale inhibitors include, but are not limited to, phosphates, phosphate esters, phosphoric acids, phosphonates, phosphonic acids, polyacrylamides, salts of acrylamido-methyl propane sulfonate/acrylic acid copolymer (AMPS/AA), phosphinated maleic copolymer (PHOS/MA), salts of a polymaleic acid/acrylic acid/acrylamido-methyl propane sulfonate terpolymer (PMA/AMPS), and combinations thereof.

e. Emulsifiers

Suitable emulsifiers include, but are not limited to, salts of carboxylic acids, products of acylation reactions between carboxylic acids or carboxylic anhydrides and amines, alkyl, acyl and amide derivatives of saccharides (alkyl-saccharide emulsifiers), and combinations thereof.

f. Water Clarifiers

Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, cationic polymers such as diallyldimethylammonium chloride (DADMAC), and combinations thereof.

g. Dispersants

Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate) and the triamine- and tetramine-polymethylene phosphonates with 2-4 methylene groups between each N atom, at least 2 of the numbers of methylene groups in each phosphonate being different. Other suitable dispersion agents include lignin or derivatives of lignin such as lignosulfonate and naphthalene sulfonic acid and derivatives, and combinations thereof.

h. Emulsion Breakers

Suitable emulsion breakers include, but are not limited to, dodecylbenzylsulfonic acid (DDBSA), the sodium salt of xylenesulfonic acid (NAXSA), epoxylated and propoxylated compounds, anionic cationic and nonionic surfactants, resins such as phenolic and epoxide resins, and combinations thereof.

i. Hydrogen Sulfide Scavengers

Suitable additional hydrogen sulfide scavengers include, but are not limited to, oxidants (e.g., inorganic peroxides such as sodium peroxide, or chlorine dioxide), aldehydes (e.g., of 1-10 carbons such as formaldehyde or glutaraldehyde or (meth)acrolein), triazines (e.g., monoethanol amine triazine, monomethylamine triazine, and triazines from multiple amines or mixtures thereof), glyoxal, and combinations thereof.

j. Gas Hydrate Inhibitors

Suitable gas hydrate inhibitors include, but are not limited to, thermodynamic hydrate inhibitors (THI), kinetic hydrate inhibitors (KHI), anti-agglomerates (AA), and combinations thereof. Suitable thermodynamic hydrate inhibitors include, but are not limited to, NaCl salt, KCl salt, $CaCl_2$ salt, $MgCl_2$ salt, $NaBr_2$ salt, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), alkyl or cyclic esters of alcohols (such as ethyl lactate, butyl lactate, methylethyl benzoate), and combinations thereof. Suitable kinetic hydrate inhibitors and anti-agglomerates include, but are not limited to, polymers and copolymers, polysaccharides (such as hydroxy-ethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, proteins, and combinations thereof.

k. Biocides

Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., bronopol and 2-2-dibromo-3-nitrilopropionamide (DBNPA)), sulfur compounds (e.g., isothiazolone, carbamates, and metronidazole), quaternary phosphonium salts (e.g., tetrakis(hydroxymethyl)phosphonium sulfate (THPS)), and combinations thereof. Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, peroxides, and combinations thereof.

l. pH Modifiers

Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include NaOH, KOH, $Ca(OH)_2$, CaO, $Na_2CO_3$, $KHCO_3$, $K_2CO_3$, $NaHCO_3$, MgO, and $Mg(OH)_2$.

m. Surfactants

Suitable surfactants include, but are not limited to, anionic surfactants, cationic surfactants, nonionic surfactants, and combinations thereof. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates, and combinations thereof. Cationic surfactants include alkyl trimethyl quaternary ammonium salts, alkyl dimethyl benzyl quaternary ammonium salts, dialkyl dimethyl quaternary ammonium salts, imidazolinium salts, and combinations thereof. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters, and combinations thereof. Also included are betaines and sultanes, amphoteric surfactants such as alkyl amphoacetates and amphodiacetates, alkyl amphopropipionates and amphodipropionates, alkyliminodiproprionate, and combinations thereof.

In certain embodiments, the surfactant may be a quaternary ammonium compound, an amine oxide, an ionic or non-ionic surfactant, or any combination thereof. Suitable quaternary amine compounds include, but are not limited to, alkyl benzyl ammonium chloride, benzyl cocoalkyl($C_{12}$-$C_{18}$)dimethylammonium chloride, dicocoalkyl ($C_{12}$-$C_{18}$)dimethylammonium chloride, ditallow dimethylammonium chloride, di(hydrogenated tallow alkyl)dimethyl quaternary ammonium methyl chloride, methyl bis(2-hydroxyethyl cocoalkyl($C_{12}$-$C_{18}$) quaternary ammonium chloride, dimethyl(2-ethyl) tallow ammonium methyl sulfate, n-dodecylbenzyldimethylammonium chloride, n-octadecylbenzyldimethyl ammonium chloride, n-dodecyltrimethylammonium sulfate, soya alkyltrimethylammonium chloride, and hydrogenated tallow alkyl (2-ethylhyexyl) dimethyl quaternary ammonium methyl sulfate.

n. Solvents

Suitable solvents include, but are not limited to, water, isopropanol, methanol, ethanol, 2-ethylhexanol, heavy aromatic naphtha, toluene, ethylene glycol, ethylene glycol monobutyl ether (EGMBE), diethylene glycol monoethyl ether, xylene, and combinations thereof. Representative polar solvents suitable for formulation with the composition include water, brine, seawater, alcohols (including straight chain or branched aliphatic such as methanol, ethanol, propanol, isopropanol, butanol, 2-ethylhexanol, hexanol, octanol, decanol, 2-butoxyethanol, etc.), glycols and derivatives (ethylene glycol, 1,2-propylene glycol, 1,3-propylene glycol, ethylene glycol monobutyl ether, etc.), ketones (cyclohexanone, diisobutylketone), N-methylpyrrolidinone (NMP), N,N-dimethylformamide and the like. Representative of non-polar solvents suitable for formulation with the composition include aliphatics such as pentane, hexane, cyclohexane, methylcyclohexane, heptane, decane, dodecane, diesel, and the like; aromatics such as toluene, xylene, heavy aromatic naphtha, fatty acid derivatives (acids, esters, amides), and the like.

In certain embodiments, the solvent is a polyhydroxylated solvent, a polyether, an alcohol, or a combination thereof.

In certain embodiments, the solvent is monoethyleneglycol, methanol, dimethyl sulfoxide (DMSO), dimethylformamide (DMF), tetrahydrofuran (THF), or a combination thereof.

In certain embodiments, a composition of the invention comprises from 0 to about 80 percent by weight of one or more solvents, based on the weight of the composition. In certain embodiments, a composition of the invention comprises from 0 to about 50 percent by weight of one or more solvents, based on the weight of the composition. In certain embodiments, a composition of the invention comprises 20%, 25%, 30%, 35%, 40%, 45%, or 50% by weight of one or more solvents, based on the weight of the composition.

o. Additional Components

Compositions made according to the invention may further include additional functional agents or additives that provide a beneficial property. Additional agents or additives will vary according to the particular scavenging composition being manufactured and its intend use as one skilled in the art will appreciate. According to one embodiment, the scavenging compositions do not contain any of the additional agents or additives.

4. SYNTHETIC METHODS

The compounds and compositions of the invention can be better understood in connection with the following synthetic schemes and methods which illustrate a means by which the compounds can be prepared.

Scheme 1

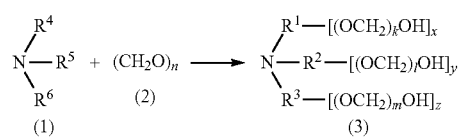

Compounds of formula (3) can be prepared as described in Scheme 1, wherein $R^1$, $R^2$, $R^3$, k, l, m, x, y, and z are as defined above. Treatment of an amine of formula (1) with an aldehyde of formula (2) will provide alkanolamine formaldehyde addition products of formula (3). $R^4$, $R^5$, and $R^6$ of formula (1) are each independently selected from hydrogen, alkyl, alkenyl, and alkynyl, provided that at least one of $R^4$, $R^5$, and $R^6$ includes at least one hydroxyl group available for reaction with the compound of formula (2). The aldehyde compound of formula (2) may be a monomeric aldehyde (e.g., formaldehyde) or a polymeric aldehyde (e.g., paraformaldehyde), wherein n ranges from, for example, 1 to 100. The compound of formula (2) can be provided as a solution, such as a 37% aqueous solution or a 50% aqueous solution.

The amine of formula (1) and the aldehyde of formula (2) may be reacted in any suitable molar ratio to provide the desired product. In certain embodiments, the amine:aldehyde reactant molar ratio may range from 1:0.25 to 1:25, particularly where paraformaldehyde is used as the aldehyde compound of formula (2). In certain embodiments, the amine:aldehyde reactant molar ratio may be 0.5:20. In certain embodiments, the amine:aldehyde reactant molar ratio may be 1:1. In certain embodiments, the amine:aldehyde reactant molar ratio may be 1:2. In certain embodiments, the amine:aldehyde reactant molar ratio may be 1:3. In certain embodiments, the amine:aldehyde reactant molar ratio may be 1:4. In certain embodiments, the amine:aldehyde reactant molar ratio may be 1:5. In certain embodiments, the amine:aldehyde reactant molar ratio may be 1:6. In certain embodiments, the amine:aldehyde reactant molar ratio may be 1:7. In certain embodiments, the amine:aldehyde reactant molar ratio may be 1:8. In certain embodiments, the amine:aldehyde reactant molar ratio may be 1:9. In certain embodiments, the amine:aldehyde reactant molar ratio may be 1:10.

In certain embodiments, compounds of formula (3) may be prepared by the addition of the aldehyde compound of formula (2) to a stirred and heated (e.g., 70-120° C., or 40-100° C.) amine of formula (1). Aqueous addition products of formula (3) may be prepared by the reaction of aqueous formalin with an amine of formula (1).

Compounds of formula (3) prepared in aqueous solution may be maintained as aqueous solutions. Alternatively, in certain embodiments, the water may be removed and replaced with a different solvent, such as monoethyleneglycol, methanol, dimethyl sulfoxide (DMSO), dimethylformamide (DMF), or tetrahydrofuran (THF).

In certain embodiments, lower molecular weight addition products of formula (3) may be prepared and may be water miscible.

Anhydrous addition products of formula (3) may be prepared by azeotropic distillation with azeotropic distillation co-solvents including, but not limited to, toluene, xylenes, cyclohexane, and heptane. The azeotropic distillation may be affected by adding 0-50% by weight of solvent to the addition products of formula (3), and thereafter distilling away the solvent to azeotropically remove water. Accordingly, in certain embodiments, the compounds of formula (3) may be substantially free of water. In certain embodiments, use of paraformaldehyde as the aldehyde compound of formula (2) may be preferred, as paraformaldehyde circumvents water removal processes (e.g., azeotropic distillation), avoids performance deterioration, and lowers manufacturing costs.

In certain embodiments, when one of $R^1$, $R^2$, and $R^3$ is hydrogen, cyclization products, such as those of formula (VII), may be prepared when compounds of formula (3) are exposed to elevated temperatures for prolonged periods of time.

In certain embodiments, the addition products may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases, the order of carrying out the foregoing reaction schemes may be varied to facilitate the reaction or to avoid unwanted reaction products.

5. PRODUCT BY PROCESS

The compounds and compositions of the invention include compounds and compositions produced by a process comprising treating an amine of formula (1), described above, with an aldehyde of formula (2), also described above. $R^4$, $R^5$, and $R^6$ of formula (1) are each independently selected from hydrogen, alkyl, alkenyl, and alkynyl, provided that at least one of $R^4$, $R^5$, and $R^6$ includes at least one hydroxyl group available for reaction with the compound of formula (2). The aldehyde compound of formula (2) may be a monomeric aldehyde (e.g., formaldehyde) or a polymeric aldehyde (e.g., paraformaldehyde), wherein n ranges from, for example, 1 to 100. The compound of formula (2) can be in solution, such as a 37% aqueous solution or a 50% aqueous solution. The amine of formula (1) and the aldehyde of formula (2) may be reacted in any suitable molar ratio to provide the desired product. In certain embodiments, the amine:aldehyde reactant molar ratio may range from 1:0.25 to 1:25, particularly where paraformaldehyde is used as the aldehyde compound of formula (2). In certain embodiments, the amine:aldehyde reactant molar ratio may be 0.5:20. In certain embodiments, the amine:aldehyde reactant molar ratio may be 1:1. In certain embodiments, the amine:aldehyde reactant molar ratio may be 1:2. In certain embodiments, the amine:aldehyde reactant molar ratio may be 1:3. In certain embodiments, the amine:aldehyde reactant molar ratio may be 1:4. In certain embodiments, the amine:aldehyde reactant molar ratio may be 1:5. In certain embodiments, the amine:aldehyde reactant molar ratio may be 1:6. In certain embodiments, the amine:aldehyde reactant molar ratio may be 1:7. In certain embodiments, the amine:aldehyde reactant molar ratio may be 1:8. In certain embodiments, the amine:aldehyde reactant molar ratio may be 1:9. In certain embodiments, the amine:aldehyde reactant molar ratio may be 1:10.

A product produced by the process may be prepared by the addition of the aldehyde compound of formula (2) to a stirred and heated (e.g., 70-120° C., or 40-100° C.) amine of formula (1). Aqueous addition products may be prepared by the reaction of aqueous formalin with an amine of formula (1).

In certain embodiments, a compound or composition of the invention includes the product of treating 1 molar equivalent of triethanolamine with 3 molar equivalents of paraformaldehyde or formaldehyde. In certain embodiments, a compound or composition of the invention includes the product of treating 1 molar equivalent of triethanolamine with 6 molar equivalents of paraformaldehyde or formaldehyde. In certain embodiments, a compound or composition of the invention includes the product of treating 1 molar equivalent of triethanolamine with 9 or 10 molar equivalents of paraformaldehyde or formaldehyde.

In certain embodiments, a compound or composition of the invention includes the product of treating 1 molar equivalent of methyldiethanolamine with 3 molar equivalents of paraformaldehyde or formaldehyde. In certain embodiments, a compound or composition of the invention includes the product of treating 1 molar equivalent of methyldiethanolamine with 6 molar equivalents of paraformaldehyde or formaldehyde. In certain embodiments, a compound or composition of the invention includes the product of treating 1 molar equivalent of methyldiethanolamine with 9 or 10 molar equivalents of paraformaldehyde or formaldehyde.

In certain embodiments, a compound or composition of the invention includes the product of treating 1 molar equivalent of diethanolamine with 3 molar equivalents of paraformaldehyde or formaldehyde. In certain embodiments, a compound or composition of the invention includes the product of treating 1 molar equivalent of diethanolamine with 6 molar equivalents of paraformaldehyde or formaldehyde. In certain embodiments, a compound or composition of the invention includes the product of treating 1 molar equivalent of diethanolamine with 9 or 10 molar equivalents of paraformaldehyde or formaldehyde.

In certain embodiments, a compound or composition of the invention includes the product of treating 1 molar equivalent of triethanolamine with an aqueous formaldehyde solution (e.g., a 37% solution). In certain embodiments, a compound or composition of the invention includes the product of treating 1 molar equivalent of methyldiethanolamine with an aqueous formaldehyde solution (e.g., a 37% solution). In certain embodiments, a compound or composition of the invention includes the product of treating 1 molar equivalent of diethanolamine with an aqueous formaldehyde solution (e.g., a 37% solution).

The products produced by the processes disclosed herein may be used neat, or prepared as compositions comprising one or more additives as described herein. The products may be used in methods of removing hydrogen sulfide and/or mercaptans from a gas or fluid, as described herein.

6. METHODS OF USE

The compounds and compositions of the invention may be used for sweetening a gas or liquid, such as a sour gas or a sour liquid. The compounds and compositions may be used for scavenging hydrogen sulfide and/or mercaptans from a gas or liquid stream by treating said stream with an effective amount of a compound or composition of the invention, as described herein. The compounds and compositions of the invention can be used in any industry where it is desirable to capture hydrogen sulfide and/or mercaptans from a gas or liquid stream. In certain embodiments, the compounds and compositions can be used in water systems, condensate/oil systems/gas systems, or any combination thereof. In certain embodiments, the compounds and compositions can be applied to a gas or liquid produced or used in the production, transportation, storage, and/or separation of crude oil or natural gas. In certain embodiments, the compounds and compositions can be applied to a gas stream used or produced in a coal-fired process, such as a coal-fired power plant. In certain embodiments, the compounds and compositions can be applied to a gas or liquid produced or used in a waste-water process, a farm, a slaughter house, a land-fill, a municipality waste-water plant, a coking coal process, or a biofuel process.

The compounds and compositions may be added to any fluid or gas containing hydrogen sulfide and/or a mercaptan, or a fluid or gas that may be exposed to hydrogen sulfide and/or a mercaptan. A fluid to which the compounds and compositions may be introduced may be an aqueous medium. The aqueous medium may comprise water, gas, and optionally liquid hydrocarbon. A fluid to which the compounds and compositions may be introduced may be a liquid hydrocarbon. The liquid hydrocarbon may be any type of liquid hydrocarbon including, but not limited to, crude oil, heavy oil, processed residual oil, bitminous oil, coker oils, coker gas oils, fluid catalytic cracker feeds, gas oil, naphtha, fluid catalytic cracking slurry, diesel fuel, fuel oil, jet fuel, gasoline, and kerosene. In certain embodiments, the gas may be a sour gas. In certain embodiments, the fluid or gas may be a refined hydrocarbon product.

A fluid or gas treated with a compound or composition of the invention may be at any selected temperature, such as ambient temperature or an elevated temperature. In certain embodiments, the fluid (e.g., liquid hydrocarbon) or gas may be at a temperature of from about 40° C. to about 250° C. In certain embodiments, the fluid or gas may be at a temperature of from −50° C. to 300° C., 0° C. to 200° C., 10° C. to 100° C., or 20° C. to 90° C. In certain embodiments, the fluid or gas may be at a temperature of 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. In certain embodiments, the fluid or gas may be at a temperature of 85° C., 86° C., 87° C., 88° C., 89° C., 90° C., 91° C., 92° C., 93° C., 94° C., 95° C., 96° C., 97° C., 98° C., 99° C., or 100° C.

The compounds and compositions of the invention may be added to a fluid at various levels of water cut. For example, the water cut may be from 0% to 100% volume/volume (v/v), from 1% to 80% v/v, or from 1% to 60% v/v. The fluid can be an aqueous medium that contains various levels of salinity. In one embodiment, the fluid may have a salinity of 0% to 25%, about 1% to 24%, or about 10% to 25% weight/weight (w/w) total dissolved solids (TDS).

The fluid or gas in which the compounds and compositions of the invention are introduced may be contained in and/or exposed to many different types of apparatuses. For example, the fluid or gas may be contained in an apparatus that transports fluid or gas from one point to another, such as an oil and/or gas pipeline. In certain embodiments, the apparatus may be part of an oil and/or gas refinery, such as a pipeline, a separation vessel, a dehydration unit, or a gas line. The fluid may be contained in and/or exposed to an apparatus used in oil extraction and/or production, such as a wellhead. The apparatus may be part of a coal-fired power plant. The apparatus may be a scrubber (e.g., a wet flue gas desulfurizer, a spray dry absorber, a dry sorbent injector, a spray tower, a contact or bubble tower, or the like). The apparatus may be a cargo vessel, a storage vessel, a holding tank, or a pipeline connecting the tanks, vessels, or processing units. In certain embodiments, the fluid or gas may be contained in water systems, condensate/oil systems/gas systems, or any combination thereof.

The compounds or compositions of the invention may be introduced into a fluid or gas by any appropriate method for ensuring dispersal of the scavenger through the fluid or gas. The compounds and compositions may be injected using mechanical equipment such as chemical injection pumps, piping tees, injection fittings, atomizers, quills, and the like. The compounds and compositions of the invention may be introduced with or without one or more additional polar or non-polar solvents depending upon the application and requirements. In certain embodiments, the compounds and compositions of the invention may be pumped into an oil and/or gas pipeline using an umbilical line. In certain embodiments, capillary injection systems can be used to deliver the compounds and compositions to a selected fluid. In certain embodiments, the compounds and compositions can be introduced into a liquid and mixed. In certain embodiments, the compounds and compositions can be injected into a gas stream as an aqueous or nonaqueous solution, mixture, or slurry. In certain embodiments, the fluid or gas may be passed through an absorption tower comprising a compound or composition of the invention.

The compounds and compositions may be applied to a fluid or gas at to provide a scavenger concentration of about 1 parts per million (ppm) to about 1,000,000 ppm, about 1 parts per million (ppm) to about 100,000 ppm, about 10 ppm to about 75,000 ppm, about 100 ppm to about 45,000 ppm, about 500 ppm to about 40,000 ppm, about 1,000 ppm to about 35,000 ppm, about 3,000 ppm to about 30,000 ppm, about 4,000 ppm to about 25,000 ppm, about 5,000 ppm to about 20,000 ppm, about 6,000 ppm to about 15,000 ppm, or about 7,000 ppm to about 10,000 ppm. The compounds and compositions may be applied to a fluid at a concentration of about 100 ppm to about 2,000 ppm, about 200 ppm to about 1,500 ppm, or about 500 ppm to about 1000 ppm. Each system may have its own requirements, and a more sour gas (e.g., containing more hydrogen sulfide) may require a higher dose rate of a compound or composition of the invention. In certain embodiments, the compounds and compositions may be applied to a fluid or gas in an equimolar amount or greater relative to hydrogen sulfide and/or mercaptans present in the fluid or gas. In certain embodiments, the compounds and compositions may be applied to a fluid or gas as a neat composition (e.g., the compounds and compositions may be used neat in a contact tower).

The hydrogen sulfide and/or mercaptan in a fluid or gas may be reduced by any amount by treatment with a compound or composition of the invention. The actual amount of residual hydrogen sulfide and/or mercaptan after treatment may vary depending on the starting amount. In certain embodiments, the hydrogen sulfide and/or mercaptan levels may be reduced to about 150 ppm by volume or less, as measured in the vapor phase, based on the volume of the liquid media. In certain embodiments, the hydrogen sulfide levels and/or mercaptan may be reduced to 100 ppm by volume or less, as measured in the vapor phase, based on the volume of the liquid media. In certain embodiments, the hydrogen sulfide and/or mercaptan levels may be reduced to 50 ppm by volume or less, as measured in the vapor phase, based on the volume of the liquid media. In certain embodiments, the hydrogen sulfide and/or mercaptan levels may be reduced to 20 ppm by volume or less, as measured in the vapor phase, based on the volume of the liquid media. In certain embodiments, the hydrogen sulfide and/or mercaptan levels may be reduced to 15 ppm by volume or less, as measured in the vapor phase, based on the volume of the liquid media. In certain embodiments, the hydrogen sulfide and/or mercaptan levels may be reduced to 10 ppm by volume or less, as measured in the vapor phase, based on the volume of the liquid media. In certain embodiments, the hydrogen sulfide and/or mercaptan levels may be reduced to 5 ppm by volume or less, as measured in the vapor phase, based on the volume of the liquid media. In certain embodiments, the hydrogen sulfide and/or mercaptan levels may be reduced to 0 ppm by volume, as measured in the vapor phase, based on the volume of the liquid media.

In certain embodiments, the compounds and compositions of the invention may be soluble in an aqueous phase such that the captured sulfur-based species will migrate into the aqueous phase. If an emulsion is present, the captured sulfur-based species can be migrated into the aqueous phase from a hydrocarbon phase (e.g., crude oil) and removed with the aqueous phase. If no emulsion is present, a water wash can be added to attract the captured sulfur-based species. In certain embodiments, the compounds and compositions of the invention can be added before a hydrocarbon (e.g., crude oil) is treated in a desalter, which emulsifies the hydrocarbon media with a water wash to extract water soluble contaminants and separates and removes the water phase from the hydrocarbon.

In certain embodiments, a water wash may be added in an amount suitable for forming an emulsion with a hydrocarbon. In certain embodiments, the water wash may be added in an amount of from about 1 to about 50 percent by volume based on the volume of the emulsion. In certain embodiments, the wash water may be added in an amount of from about 1 to about 25 percent by volume based on the volume of the emulsion. In certain embodiments, the wash water may be added in an amount of from about 1 to about 10 percent by volume based on the volume of the emulsion. In certain embodiments, the amount of hydrocarbon may be present in an amount of from about 50 to about 99 percent by volume based on the volume of the emulsion. In certain embodiments, the hydrocarbon may be present in an amount of from about 75 to about 99 percent by volume based on the volume of the emulsion. In certain embodiments, the hydrocarbon may be present in an amount of from about 90 to about 99 percent by volume based on the volume of the emulsion.

The water wash and hydrocarbon may be emulsified by any conventional manner. In certain embodiments, the water wash and hydrocarbon may be heated and thoroughly mixed to produce an oil-in-water emulsion. In certain embodiments, the water wash and hydrocarbon may be heated at a temperature in a range of from about 90° C. to about 150° C. The water wash and hydrocarbon may be mixed in any conventional manner, such as an in-line static mixer or an in-line mix valve with a pressure drop of about 0.2 to about 2 bar depending on the density of the hydrocarbon. The emulsion may be allowed to separate, such as by settling, into an aqueous phase and an oil phase. In certain embodiments, the aqueous phase may be removed. In another embodiment, the aqueous phase may be removed by draining the aqueous phase.

Optionally, demulsifiers may be added to aid in separating water from the hydrocarbon. In certain embodiments, the demulsifiers include, but are not limited to, oxyalkylated organic compounds, anionic surfactants, nonionic surfactants or mixtures of these materials. The oxyalkylated organic compounds include, but are not limited to, phenol-formaldehyde resin ethoxylates and alkoxylated polyols. The anionic surfactants include alkyl or aryl sulfonates, such as dodecylbenzenesulfonate. These demulsifiers may be added in amounts to contact the water from about 1 to about 1000 ppm by weight based on the weight of the hydrocarbon.

The compounds, compositions, methods, and processes of the invention will be better understood by reference to the following examples, which are intended as an illustration of and not a limitation upon the scope of the invention.

7. EXAMPLES

The foregoing may be better understood by reference to the following examples, which are presented for purposes of illustration and are not intended to limit the scope of the invention.

a. Compounds and Compositions

Example 1

Triethanolamine Formaldehyde Addition Product
(3:1 Aldehyde:Amine Mole Ratio)

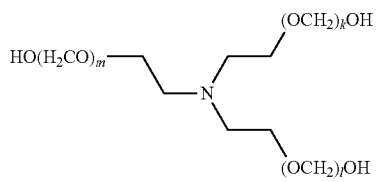

Paraformaldehyde and triethanolamine (TEA) were charged in a 3:1 mole ratio into a 1000 mL four-neck round-bottom flask and heated with stirring to 80-100° C. slowly over a period of 1.5 hours under an inert atmosphere to prevent discoloration. After the paraformaldehyde was completely dissolved and/or reacted the heating was stopped and cooled to room temperature to yield triethanolamine formaldehyde addition product in quantitate yield.

Example 2

Triethanolamine Formaldehyde Addition Product
(6:1 Aldehyde:Amine Mole Ratio)

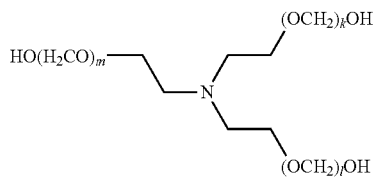

Paraformaldehyde and triethanolamine (TEA) were charged in a 6:1 mole ratio into a 1000 mL four-neck round-bottom flask and heated with stirring to 80-100° C. slowly over a period of 2.0 hours under an inert atmosphere to prevent discoloration. After the paraformaldehyde was completely dissolved and/or reacted the heating was stopped and cooled to room temperature to yield triethanolamine formaldehyde addition product in quantitate yield.

Example 3

Triethanolamine Formaldehyde Addition Product
(10:1 Aldehyde:Amine Mole Ratio)

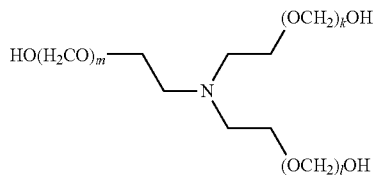

Paraformaldehyde was slowly charged in portions to triethanolamine (TEA) in a 1000 mL four-neck round-bottom flask with stirring and heating to 90-100° C. under an inert atmosphere to prevent discoloration until a molar ratio of 10:1 was met. At no time did the reaction temperature exceed 100° C. After the paraformaldehyde was completely dissolved and/or reacted the heating was stopped and cooled to room temperature to yield triethanolamine formaldehyde addition product in quantitate yield.

Example 4

Methyldiethanolamine Formaldehyde Addition
Product (2:1 Aldehyde:Amine Mole Ratio)

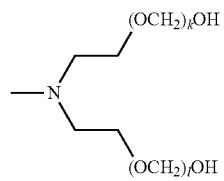

Paraformaldehyde and methyldiethanolamine (MDEA) were charged in a 2:1 mole ratio into a 1000 mL four-neck round-bottom flask and heated with stirring to 80-100° C. slowly over a period of 1.5 hours under an inert atmosphere to prevent discoloration. After the paraformaldehyde was completely dissolved and/or reacted the heating was stopped and cooled to room temperature to yield methyldiethanolamine formaldehyde addition product in quantitate yield.

Example 5

Methyldiethanolamine Formaldehyde Addition
Product (4:1 Aldehyde:Amine Mole Ratio)

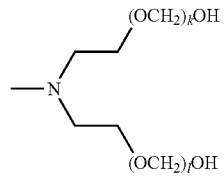

Paraformaldehyde and methyldiethanolamine (MDEA) are charged in a 4:1 mole ratio into a 1000 mL four-neck round-bottom flask and heated with stirring to 70-90° C. slowly over a period of 2.0 hours under an inert atmosphere to prevent discoloration. After the paraformaldehyde is completely dissolved and/or reacted the heating is stopped and cooled to room temperature to yield methyldiethanolamine formaldehyde addition product in quantitate yield.

Example 6

Methyldiethanolamine Formaldehyde Addition
Product (6:1 Aldehyde:Amine Mole Ratio)

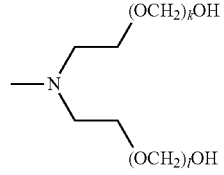

Paraformaldehyde is slowly charged in portions to methyldiethanolamine (MDEA) in a 1000 mL four-neck round-bottom flask with stirring and heating to 90-100° C. under an inert atmosphere to prevent discoloration until a molar ratio of 6:1 is met. At no time does the reaction temperature exceed 100° C. After the paraformaldehyde is completely dissolved and/or reacted the heating is stopped and cooled to room temperature to yield methyldiethanolamine formaldehyde addition product in quantitate yield.

Example 7

Triethanolamine Formaldehyde Addition Product from Aqueous Formaldehyde and Triethanolamine (3:1 Aldehyde:Amine Mole Ratio)

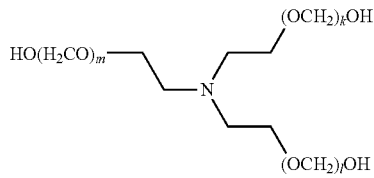

250 g of an aqueous formaldehyde solution (37%) was charged to a four-neck 100 mL flask and stirred. 150 g of triethanolamine (TEA) was added at a constant rate maintaining a reaction temperature of less than 90° C. The reaction was mildly exothermic. After the TEA addition was complete, 5-10% of toluene was added to the reaction vessel and heated with stirring to the temperature where toluene and water azeotropically distilled (85-90° C.). After the quantitative amount of water was removed from the reaction by azeotropic distillation, the reaction temperature was raised to 95-115° C. such that any remaining toluene was distilled and removed, providing the triethanolamine formaldehyde addition product in quantitative yield.

Example 8

Methyldiethanolamine Formaldehyde Addition Product from Aqueous Formaldehyde and Methyldiethanolamine (2:1 Aldehyde:Amine Mole Ratio)

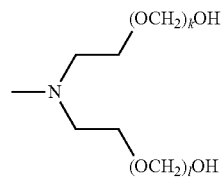

164 g of an aqueous formaldehyde solution (37%) is charged to a four-neck 100 mL flask and stirred. 119 g of methyldiethanolamine (MDEA) is added at a constant rate maintaining a reaction temperature of less than 90° C. The reaction is mildly exothermic. After the MDEA addition is complete, 5-10% of toluene is added to the reaction vessel and heated with stirring to the temperature where toluene and water are azeotropically distilled (85-90° C.). After the quantitative amount of water is removed from the reaction by azeotropic distillation, the reaction temperature is raised to 95-115° C. such that any remaining toluene is distilled and removed, providing the anhydrous methyldiethanolamine formaldehyde addition product in quantitative yield.

Example 9

Diethanolamine Formaldehyde Addition Product from Paraformaldehyde and Diethanolamine (2:1 Aldehyde:Amine Mole Ratio & 3:1 Aldehyde:Amine Mole Ratio)

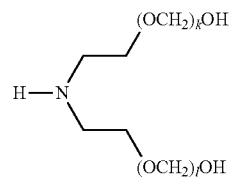

Paraformaldehyde is dispersed in toluene (5-10 wt. %) and heated to 85-90° C. while stirring. Diethanolamine is added at a constant rate maintaining a reaction temperature of less than 90° C. After all the diethanolamine is added, the reaction is allowed to continue to heat at 85-90° C. for 30-35 minutes. The reaction temperature is increased to 100° C. where toluene and water of reaction are azeotropically distilled (85-90° C.). After the quantitative amount of water is removed from the reaction by azeotropic distillation, the reaction temperature is raised to 95-115° C. such that any remaining toluene is distilled and removed, providing the diethanolamine formaldehyde addition product in quantitative yield.

Care is taken to avoid temperatures of more than 120° C. to avoid degradation of the addition product. Sparging the fluids with an inert gas may be used to remove the last traces of toluene. Analysis may indicate the presence of diethanolamine formaldehyde addition product, as well as cyclizied products of formula (VII), shown above.

Example 10

Diethanolamine Formaldehyde Addition Product from Paraformaldehyde and Diethanolamine

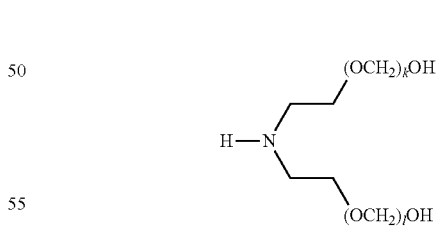

Paraformaldehyde was heated to 70-75° C. while stirring. Diethanolamine was added at a constant rate maintaining a reaction temperature of less than 75° C. After all the diethanolamine was added, the reaction was allowed to continue to stir at 75° C. for 30-35 minutes. The diethanolamine formaldehyde addition product was isolated in quantitative yield.

Care was taken to avoid temperatures of more than 75° C. to avoid degradation and/or cyclization of the addition products. Analysis indicated the presence of diethanolamine formaldehyde addition product, as well as minimal cyclicl-
ized product of formula (VII), shown above.

Example 11

Diethanolamine Formaldehyde Addition Product
from Aqueous Formaldehyde and Diethanolamine
(2:1 Aldehyde:Amine Mole Ratio & 3:1
Aldehyde:Amine Mole Ratio)

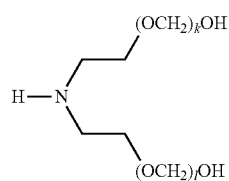

An aqueous formaldehyde solution (37%) is mixed with toluene (5-10 wt. %) and heated to 85-90° C. while stirring. Diethanolamine is added at a constant rate maintaining a reaction temperature of less than 90° C. After all the diethanolamine is added, the reaction continues to heat at 85-90° C. for 30-35 minutes. The reaction temperature is increased to 100° C. where toluene and water of reaction azeotropically distill (85-90° C.). After the quantitative amount of water is removed from the reaction by azeotropic distillation, the reaction temperature is raised to 95-115° C. such that any remaining toluene is distilled and removed from the addition product, providing the product in quantitative yield.

Care is taken to avoid temperatures of more than 120° C. to avoid degradation of the addition product. Sparging the fluids with an inert gas may be used to remove the last traces of toluene. Analysis may indicate the presence of diethanolamine formaldehyde addition product, as well as cyclicized product of formula (VII), as shown above.

Example 12

Dimethylmonoethanolamine Formaldehyde
Addition Product from Paraformaldehyde and
Dimethylmonoethanolamine (1:1 Aldehyde:Amine
Mole Ratio)

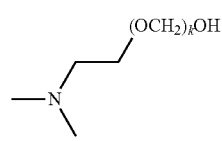

b. Scavenging Results

Formulations of the compounds and compositions of the invention were prepared and evaluated for hydrogen sulfide scavenging ability. The formulations prepared include neat formulations of the alkanolamine formaldehyde addition products; formulations of alkanolamine formaldehyde addition products and one or more solvents; formulations of alkanolamine formaldehyde addition products and one or more surfactant compounds; and combinations thereof. Table 1 shows Formulations prepared and evaluated for scavenging ability.

TABLE 1

| Formulation | Formulation Description |
|---|---|
| Formulation 1 | Example 1 (3:1 Formaldehyde:Triethanolamine Mole Ratio), formulated with 35% water, by weight |
| Formulation 2 | Example 1 (3:1 Formaldehyde:Triethanolamine Mole Ratio) formulated with 28% water, by weight |
| Formulation 3 | Example 3 (10:1 Formaldehyde:Triethanolamine Mole Ratio) formulated with 38% water, by weight |
| Formulation 4 | Example 3 (10:1 Formaldehyde:Triethanolamine Mole Ratio) formulated with 20% monoethylene glycol, by weight |
| Formulation 5 | Example 1 (3:1 Formaldehyde:Triethanolamine Mole Ratio) that is solvent free |
| Formulation 6 | Example 1 (3:1 Formaldehyde:Triethanolamine Mole Ratio) formulated with water |
| Formulation 7 | Example 2 (6:1 Formaldehyde:Triethanolamine Mole Ratio) formulated with water |
| Formulation 8 | Example 3 (9:1 Formaldehyde:Triethanolamine Mole Ratio) formulated with water |
| Formulation 9 | Example 1 (3:1 Formaldehyde:Triethanolamine Mole Ratio) formulated with 5% cocoamine sulfate quat, and 35% water, by weight |
| Formulation 10 | Example 3 (10:1 Formaldehyde:Triethanolamine Mole Ratio) formulated with 20% ethylene glycol, 50% water, and 5% cocoamine methylsulfate quat, by weight |
| Formulation 11 | Example 3 (10:1 Formaldehyde:Triethanolamine Mole Ratio) formulated with 20% ethylene glycol, 40% water, and 5% cocoamine chloride quat, by weight |
| Formulation 12 | Example 3 (10:1 Formaldehyde:Triethanolamine Mole Ratio) formulated with 20% ethylene glycol, and 6.5% cocoamine methylsulfate quat, by weight |
| Formulation 13 | Example 3 (10:1 Formaldehyde:Triethanolamine Mole Ratio) formulated with 20% ethylene glycol, and 5% cocoamine chloride quat, by weight |
| Formulation 14 | Example 1 (3:1 Formaldehyde:Triethanolamine Mole Ratio) formulated with 8% cocoamine methyl sulfate quat, and 28% water, by weight |
| Formulation 15 | Example 1 (3:1 Formaldehyde:Triethanolamine Mole Ratio) formulated with 7% cocoamine chloride quat, and 25% water, by weight |
| Formulation 16 | Example 1 (3:1 Formaldehyde:Triethanolamine Mole Ratio) formulated with 6% cocoamine benzyl chloride quat, and 35% water, by weight |

Table 2 shows the dose response profile of the product of Example 1 formulated with 35% water to aid in the dispersion of the scavenger (Formulation 1). The test was conducted using kerosene at 22° C. containing 1200 ppm of hydrogen sulfide in the vapor. The amount of hydrogen sulfide in the vapor was measured using a ½ full 1 quart container using Draeger Tubes to measure the amount of hydrogen sulfide in the vapor. Formulation 1 was added to the bottle followed by the kerosene containing $H_2S$. The samples were vigorously shaken for 30 seconds and then set at room temperature for 2 hours. After 2 hours, the sample was shaken vigorously for 30 seconds and then tested with a Draeger tube.

TABLE 2

| Sample Description | Initial $H_2S$ ppm | Final $H_2S$ ppm | Dose ppm | Dose Ratio | % Reduction |
|---|---|---|---|---|---|
| Untreated | 1200 | — | — | 0 | — |
| Formulation 1 | 1200 | 800 | 120 | 0.1 | 33.3 |
| Formulation 1 | 1200 | 800 | 240 | 0.2 | 33.3 |
| Formulation 1 | 1200 | 650 | 360 | 0.3 | 45.8 |
| Formulation 1 | 1200 | 575 | 480 | 0.4 | 52.1 |
| Formulation 1 | 1200 | 500 | 600 | 0.5 | 58.3 |
| Formulation 1 | 1200 | 300 | 1200 | 1 | 75.0 |

Table 3 shows comparison of different hydrogen sulfide scavenging formulations at fixed doses in kerosene. Formulation 2 is the product of Example 1 (3:1 Aldehyde:Amine Mole Ratio) formulated with 28% water. Formulation 3 is the product of Example 3 (10:1 Aldehyde:Amine Mole Ratio) formulated with 38% water. Formulation 4 is the product of Example 3 (10:1 Aldehyde:Amine Mole Ratio) formulated with 20% monoethylene glycol. Formulation 5 is the product of Example 1 (3:1 Aldehyde:Amine Mole Ratio) that is solvent free.

The tests were conducted using kerosene that contained 1300 ppm of hydrogen sulfide in the vapor. The amount of hydrogen sulfide in the vapor was measured using a ½ full 1 quart container using Draeger Tubes to measure the amount of hydrogen sulfide in the vapor. The formulations were each added to a fresh bottle followed by 500 mL of kerosene containing $H_2S$. The samples were sealed and vigorously shaken for 30 seconds and then set at room temperature for 1.5 hours. After 2 hours the samples were shaken vigorously for 30 seconds and then tested with a Draeger tube.

TABLE 3

| Sample Description | Initial $H_2S$ ppm | Final $H_2S$ ppm | Dose ppm | Dose Ratio | % Reduction |
|---|---|---|---|---|---|
| Untreated | 1300 | — | — | 0 | — |
| Formulation 2 | 1300 | 500 | 650 | 0.5 | 61.5 |
| Formulation 3 | 1300 | 600 | 650 | 0.5 | 53.8 |
| Formulation 4 | 1300 | 800 | 650 | 0.5 | 38.5 |
| Formulation 5 | 1300 | 700 | 650 | 0.5 | 46.1 |

Table 4 shows comparison of Formulations 6-8 at a 0.05 dose rose ratio in fuel oil heated to 90° C. Formulation 6 is the product of Example 1 formulated with water. Formulation 7 is the product of Example 2 formulated with water. Formulation 8 is the product of the reaction of 9 moles of formaldehyde with 1 mole of triethanolamine, and contains water.

The tests were conducted using fuel oil that contained 2400 ppm of hydrogen sulfide in the vapor. The amount of hydrogen sulfide in the vapor was measured using a ½ full 1 quart container using Draeger Tubes to measure the amount of hydrogen sulfide in the vapor. The formulations were each added to a fresh sample container followed by 500 mL of the fuel oil containing $H_2S$. The samples were sealed and vigorously shaken for 30 seconds and then placed in an oven set at 90° C. for 2 hours. After 2 hours the samples were shaken vigorously for 30 seconds and then tested with a Draeger tube.

TABLE 4

| Sample Description | Initial $H_2S$ ppm | Final $H_2S$ ppm | Dose ppm | Dose Ratio | % Reduction |
|---|---|---|---|---|---|
| Untreated | 2400 | — | — | 0 | — |
| Formulation 6 | 2400 | 700 | 120 | 0.05 | 71.0 |
| Formulation 7 | 2400 | 1000 | 120 | 0.05 | 58.0 |
| Formulation 8 | 2400 | 1375 | 120 | 0.05 | 43.0 |

Table 5 shows comparison of Formulations 6-8 at a dose ratio of 0.1 in water at 22° C. The water containing 1000 ppm of $H_2S$ was placed in a 500 mL bottle with a stir bar and the $H_2S$ was measured after 15 minutes. The formulations were each added to a fresh bottle and 250 mL of water was added with stirring. After 15 minutes the cap was removed and the vapor space $H_2S$ measured using a Draeger tube.

TABLE 5

| Sample Description | Initial $H_2S$ ppm | Final $H_2S$ ppm | Dose ppm | Dose Ratio | % Reduction |
|---|---|---|---|---|---|
| Untreated | 1000 | — | — | 0 | — |
| Formulation 6 | 1000 | 425 | 100 | 0.1 | 57.5 |
| Formulation 7 | 1000 | 675 | 100 | 0.1 | 32.5 |
| Formulation 8 | 1000 | 800 | 100 | 0.1 | 20.0 |

Table 6 shows the dose response profile of the product of Example 1 formulated with 35% water and a quaternary amine surfactant (Formulation 9). The test was conducted using kerosene at 22° C. containing 1100 ppm of hydrogen sulfide in the vapor. The amount of hydrogen sulfide in the vapor was measured using a ½ full 1 quart container using Draeger Tubes to measure the amount of hydrogen sulfide in the vapor. Formulation 9 (3:1 Formaldehyde:TEA, formulated with 5% cocoamine sulfate quat with 35% water) was added to a fresh bottle followed by 500 mL of the kerosene containing $H_2S$. The samples were sealed and vigorously shaken for 30 seconds and then set at room temperature for 2 hours. After 2 hours the sample was shaken vigorously for 30 seconds and then tested with a Draeger tube.

TABLE 6

| Sample Description | Initial $H_2S$ ppm | Final $H_2S$ ppm | Dose ppm | Dose Ratio | % Reduction |
|---|---|---|---|---|---|
| Untreated | 1100 | — | — | 0 | — |
| Formulation 9 | 1100 | 220 | 110 | 0.1 | 72.7 |
| Formulation 9 | 1100 | 40 | 220 | 0.2 | 96.4 |
| Formulation 9 | 1100 | 10 | 330 | 0.3 | 99.1 |
| Formulation 9 | 1100 | 5 | 440 | 0.4 | 99.5 |
| Formulation 9 | 1100 | 2 | 550 | 0.5 | 99.8 |

Table 7 shows the dose response profile of the product of Example 3 formulated with 20% ethylene glycol, 50% water, and 5% quaternary amine (Formulation 10). The test was conducted using kerosene at 22° C. containing 2100 ppm of hydrogen sulfide in the vapor. The amount of hydrogen sulfide in the vapor was measured using a ½ full 1 quart container using Draeger Tubes to measure the amount of hydrogen sulfide in the vapor. Formulation 10 (10:1 Formaldehyde:TEA, formulated with 20% ethylene glycol, 50% water, and 5% cocoamine methylsulfate quat) was added to a fresh bottle followed by 500 mL of the kerosene containing $H_2S$. The samples were sealed and vigorously shaken for 30 seconds and then set at room temperature for 2 hours. After 2 hours the sample was shaken vigorously for 30 seconds and then tested with a Draeger tube.

TABLE 7

| Sample Description | Initial $H_2S$ ppm | Final $H_2S$ ppm | Dose ppm | Dose Ratio | % Reduction |
|---|---|---|---|---|---|
| Untreated | 2100 | — | — | 0 | — |
| Formulation 10 | 2100 | 220 | 210 | 0.1 | 89.5 |
| Formulation 10 | 2100 | 70 | 420 | 0.2 | 96.7 |
| Formulation 10 | 2100 | 20 | 630 | 0.3 | 99.0 |
| Formulation 10 | 2100 | 5 | 840 | 0.4 | 99.8 |

Table 8 shows hydrogen sulfide scavenging ability of Formulations 10-13 at a dose ratio of 1.0. The tests were conducted using kerosene at 35° C. containing 1900 ppm of hydrogen sulfide in the vapor; and at a 1.0 dose ratio for each formulation and a residence time of 30 minutes.

TABLE 8

| Sample Description | Initial H$_2$S ppm | Final H$_2$S ppm | Dose ppm | Dose Ratio | % Reduction |
|---|---|---|---|---|---|
| Untreated | 1900 | — | — | 0 | — |
| Formulation 10 | 1900 | 0 | 1900 | 1 | 100.0 |
| Formulation 11 | 1900 | 0 | 1900 | 1 | 100.0 |
| Formulation 12 | 1900 | 0 | 1900 | 1 | 100.0 |
| Formulation 13 | 1900 | 10 | 1900 | 1 | 99.5 |

Table 9 shows hydrogen sulfide scavenging ability of Formulations 10, 11, 14, and 15 at a dose ratio of 0.5. The tests were conducted using kerosene at 22° C. containing 2100 ppm of hydrogen sulfide in the vapor; and at a 0.5 dose ratio for each formulation and a residence time of 1.25 hours.

TABLE 9

| Sample Description | Initial H$_2$S ppm | Final H$_2$S ppm | Dose ppm | Dose Ratio | % Reduction |
|---|---|---|---|---|---|
| Untreated | 2100 | — | — | 0 | — |
| Formulation 10 | 2100 | 0 | 1050 | 0.5 | 100.0 |
| Formulation 11 | 2100 | 70 | 1050 | 0.5 | 96.7 |
| Formulation 14 | 2100 | 10 | 1050 | 0.5 | 99.5 |
| Formulation 15 | 2100 | 220 | 1050 | 0.5 | 89.5 |

Table 10 shows the dose response profile of Formulation 16 in fuel oil at 90° C., ca. 16 hours. The tests show excellent performance of Formulation 16 for scavenging hydrogen sulfide from the fuel oil.

TABLE 10

| Sample Description | Initial H$_2$S ppm | Dose ppm | Dose Ratio | Amt H$_2$S Reduced | % Reduction |
|---|---|---|---|---|---|
| Formulation 16 | 2000 | 600 | 0.3 | 1990 | 99.5 |
| Formulation 16 | 2000 | 1200 | 0.6 | 1998 | 99.9 |
| Formulation 16 | 2000 | 1800 | 0.9 | 2000 | 100.0 |
| Formulation 16 | 2000 | 2400 | 1.2 | 2000 | 100.0 |

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety.

What is claimed is:

1. A compound of formula (I),

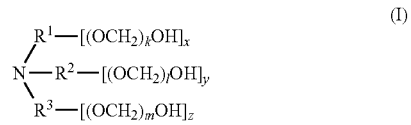

wherein
x is 1, y is 1, z is 0, R$^1$ and R$^2$ are each alkylenyl, and R$^3$ is hydrogen, and
k, l, and m are each independently an integer selected from the group consisting of 0 to 25, wherein k+l+m is >0.

2. A compound of formula (I),

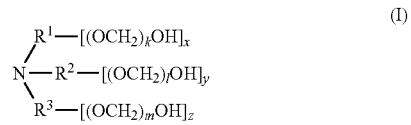

wherein x is 1, y is 1, z is 0, R$^1$ and R$^2$ are each C$_2$-alkylenyl, and R$^3$ is hydrogen, further wherein k, l, and m are each independently an integer selected from the group consisting of 0 to 25, wherein k+l+m is >0.

3. A compound of formula (I),

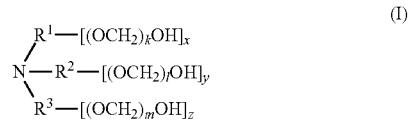

wherein x is 1, y is 1, z is 0, R$^1$ and R$^2$ are each unsubstituted C$_2$-alkylenyl, and R$^3$ is hydrogen, further wherein k, l, and m are each independently an integer selected from the group consisting of 0 to 25, wherein k+l+m is >0.

* * * * *